(12) United States Patent
Wu et al.

(10) Patent No.: US 6,951,971 B1
(45) Date of Patent: Oct. 4, 2005

(54) METHOD OF MAKING WATER STRESS OR SALT STRESS TOLERANT TRANSGENIC CEREAL PLANTS

(75) Inventors: Ray J. Wu, Ithaca, NY (US); Tuan-Hua David Ho, Chesterfield, MO (US)

(73) Assignees: Cornell Research Foundation, Inc., Ithaca, NY (US); Washington University, St. Louis, MO (US)

( * ) Notice: Subject to any disclaimer, the term of this patent is extended or adjusted under 35 U.S.C. 154(b) by 0 days.

(21) Appl. No.: 09/350,393

(22) Filed: Jul. 9, 1999

(51) Int. Cl.[7] .......................... C12N 15/82; C12N 15/29
(52) U.S. Cl. .................. 800/289; 800/320; 800/320.1; 800/320.2; 800/320.3; 800/293; 800/294; 435/468; 435/469; 435/470
(58) Field of Search ............................ 435/320.1, 419, 435/468, 469, 470; 800/278, 298, 289, 320, 800/320.1, 320.2, 320.3, 293, 294

(56) References Cited

U.S. PATENT DOCUMENTS

| | | | |
|---|---|---|---|
| 5,563,324 A | 10/1996 | Tarczynski et al. | |
| 5,595,896 A | 1/1997 | Coruzzi et al. | |
| 5,639,950 A | 6/1997 | Verma et al. | |
| 5,731,419 A | 3/1998 | Sarhan et al. | |
| 5,780,709 A | 7/1998 | Adams et al. | |

FOREIGN PATENT DOCUMENTS

| | | |
|---|---|---|
| EP | 0 864 650 A2 | 9/1998 |
| JP | 10-286034 | 10/1998 |

OTHER PUBLICATIONS

Xu et al, "Expression of a Late Embryogenesis Abundant Protein Gene, HVA1, from Barley Confers Tolerance to Water Deficit and Salt Stress in Transgenic Rice", 1996, Plant Physiol vol. 110, pp. 249-257.*

Shen et al. Modular nature of abscisic acid (ABA) response complexes: composite promoter units that are necessary and sufficient for ABA induction of gene expression in barley. The Plant Cell, vol. 8, pp. 1107-1119.*

Shen et al. Functional dissection of an abscisic acid (ABA)-inducible gene reveals two independent ABA-responsive complexes each containing a G-box and a novel cis-acting element. The Plant Cell, vol. 7, pp. 295-307.*

Wu et al. Production of transgenic rice plants that are resistant to insect pests and fungal diseases or to water and salt stress, Abstract 113, General Meeting of The International Program on Rice Biotechnology, Sep. 15-17, 1997.*

Lee J. et al. Expression of Arabidopsis CBFI Regulated by an ABA/stress Inducible Promoter in Transgenic Tomato Confers Stress Tolerance Without Affecting Yield, Plant Cell Environ 26:1181-1190, 2003.*

Su J. et al. Dehydration-stress-regulated transgene expression in stably transformed rice plants Plant Physiol. Jul. 1998;117(3):913-22.*

Lu C. et al. Three novel MYB proteins with one DNA binding repeat mediate sugar and hormone regulation of alpha-amylase gene expression. Plant Cell. Aug. 2002;14(8):1963-80.*

Odell J. et a1. Identification of DNA sequences required for activity of the cauliflower mosaic virus 35S promoter. Nature. Feb. 28-Mar. 6, 1985;313(6005):810-2.*

Gomez-Cadenas A. et al. An abscisic acid-induced protein kinase, PKABA1, mediates abscisic acid-suppressed gene expression in barley aleurone layers. Proc Natl Acad Sci U S A. Feb. 16, 1999;96(4):1767-72.*

Qu Rong Da et al, in *CRRN, Chinese Rice Research Newsletter,* 4(2):1-2, ISSN:1005-4111 (Abstract) (1996).

Skriver et al., "Cis-acting DNA Elements Responsive to Gibberellin and Its Antagonist Abscisic Acid," *Proc. Natl. Acad. Sci. USA,* 88:7266-7270 (1991).

Vilardell et al., "Regulation of the Maize *rab17* Gene Promoter in Transgenic Heterologous Systems," *Plant Molecular Biology,* 17:985-993 (1991).

Igarashi et al., "Characterization of the Gene for $\Delta^1$-Pyrroline-5-Carboxylate Synthetase and Correlation Between the Expression of the Gene and Salt Tolerance in *Oryza sativa* L.," *Plant Molecular Biology,* 33:857-865 (1997).

Moons et al., "An Abscisic-Acid- and Salt-Stress-Responsive Rice cDNA from a Novel Plant Gene Family," *Planta,* 202:443-454 (1997).

Moons et al., "Antagonistic Effects of Abscisic Acid and Jasmonates on Salt Stress-Inducible Transcripts in Rice Roots," *The Plant Cell,* 9:2243-2259 (1997).

Su et al., "Dehydration-Stress-Regulated Transgene Expression in Stably Transformed Rice Plants," Plant Physiol., 117:913-922 (1998).

Cheng et al., "Development of Transgenic Cereal Crop Plants that are Tolerant to High Salt, Drought and Low Temperature," *Frontiers in Biology: The Challenge of Biodiversity, Biotechnology and Sustainable Agriculture,* Chou et al., Eds., Academia Sinica, Taipei, pp. 115-122 (1998).

(Continued)

*Primary Examiner*—Cynthia Collins
(74) *Attorney, Agent, or Firm*—Nixon Peabody LLP

(57) ABSTRACT

The present invention relates to a method for conferring tolerance to salt stress and drought stress in a monocot plant including transforming the monocot plant with an expression cassette comprising at least one ABRC unit, a minimal promoter, and a DNA molecule that increases tolerance to salt stress and drought stress in plants, wherein the at least one ABRC unit, the minimal promoter, and a DNA molecule are operably linked together to permit expression of the DNA molecule. The present invention also relates to a transgenic monocot plant transformed with a DNA molecule that increases tolerance to salt stress and drought stress operably linked to at least one ABRC unit and a minimal promoter.

12 Claims, 10 Drawing Sheets

OTHER PUBLICATIONS

Wu et al., "Production of Transgenic Rice Plants that are Resistant to Insect Pests and Fungal Diseases or to Water and Salt Stress," *General Meeting of the International Program on Rice Biotechnology,* Sep. 15-19, 1997, Malacca, Malaysia.

Shen et al., "Modular Nature of Abscisic Acid (ABA) Response Complexes: Composite Promoter Units That Are Necessary and Sufficient for ABA Induction of Gene Expression in Barley," *The Plant Cell* 8:1107-1119 (1996).

Shen et al., "Functional Dissection of an Abscisic Acid (ABA)-Inducible Gene Reveals Two Independent ABA-Responsive Complexes Each Containing a G-Box and a Novel *cis*-Acting Element," *The Plant Cell* 7:295-307 (1995).

* cited by examiner

METHOD OF MAKING WATER STRESS OR SALT STRESS TOLERANT TRANSGENIC CEREAL PLANTS

FIELD OF THE INVENTION

The present invention relates to transgenic cereal plants which are transformed with an expression cassette including at least one ABRC unit, a minimal promoter, and a DNA molecule that increases tolerance to salt stress and drought stress in plants.

BACKGROUND OF THE INVENTION

Environmental stresses, such as drought, increased salinity of soil, and extreme temperature, are major factors in limiting plant growth and productivity. The worldwide loss in yield of three major cereal crops, rice, maize (corn), and wheat due to water stress (drought) has been estimated to be over ten billion dollars annually. Drought and soil salinity are the most serious environmental stresses that limit plant growth and crop productivity (Boyer, "Plant Productivity and Environment," Science, 218:443–448 (1982); Le Rudulier et al., "Molecular Biology of Osmoregulation," Science, 224:1064–1068 (1984)). Of the 4,870 million hectares of agricultural land in the world, 930 million (19% of total) are salt-affected areas (FAO Quarterly Bulletin of Statistics, Vol. 9¾ (1996)). Moderate levels of salt content in the soil (such as 50 mM) cause a substantial decrease in the yield of crops. High levels of salt in the soil (higher than 100 or 150 mM) are not at all suitable for planting most cereal crops. Approximately 5.2% of the agricultural lands are under drought stress (FAO Quarterly Bulletin of Statistics, Vol. 9¾ (1996)), and the loss of crop yield is also very significant.

In practical terms, rice is the most important crop, because a high percentage of the world's population depends on it for their staple food. Together with wheat and corn, these three cereal crops constitute the major source of food and calories to feed the people. With an increase in population and a decrease in arable land, there is a real possibility of a food shortage by the year 2030. Therefore, it is essential to fully utilize plant biotechnology to improve plants and produce more food.

Breeding of stress-tolerant crop cultivars represents a promising strategy to tackle these problems (Epstein et al., "Saline Culture of Crops: A Genetic Approach," Science, 210:399–404 (1980)). However, conventional breeding is a slow process for generating crop varieties with improved tolerance to stress conditions. Limited germplasm resources for stress tolerance and incompatibility in crosses between distantly related plant species are additional problems encountered in conventional breeding. Recent progress in plant genetic transformation and availability of potentially useful genes characterized from different sources make it possible to generate stress-tolerant crops using transgenic approaches (Tarczynski et al., "Stress Protection of Transgenic Tobacco by Production of the Osmolyte Mannitol," Science, 259:508–510 (1993); Pilon-Smits et al., "Improved Performance of Transgenic Fructan-Accumulating Tobacco Under Drought Stress," Physiol. Plant, 107:125–130 (1995)). Transformation of cereal plants with agronomically useful genes that increase tolerance to abiotic stress is one important way to minimize yield loss. For example, it would be highly desirable to produce transgenic rice plants that can give reasonable yield when grown in marginal or waste lands that contain relatively high levels of salt, such as 100–150 mM, in the soil.

Characterization and cloning of plant genes that confer stress tolerance remains a challenge. Genetic studies revealed that tolerance to drought and salinity in some crop varieties is principally due to additive gene effects (Akbar et al., "Breeding For Soil Stress," In Progress in Rainfed Lowland Rice, International Rice Research Institute, manila, Philippines, pp. 263–272 (1986); Akbar et al., "Genetics of Salt Tolerance in Rice," In Rice Genetics, International Rice Research Institute, Manila, Philippines, pp. 399–409 (1986)). However, the underlying molecular mechanism for the tolerance has never been revealed. Physiological and biochemical responses to high levels of ionic or nonionic solutes and decreased water potential have been studied in a variety of plants. Based on accumulated experimental observations and theoretical consideration, one suggested mechanism that may underlie the adaptation or tolerance of plants to osmotic stresses is the accumulation of compatible, low molecular weight osmolytes such as sugar alcohols, special amino acids, and glycine betaine (Greenway et al., "Mechanisms of Salt Tolerance in Nonhalophytes," Annu. Rev. Plant Physiol., 31: 149–190 (1980); Yancey et al., "Living With Water Stress: Evolution of Osmolyte System," Science, 217: 1214–1222 (1982)). In particular, proline level is known to increase in a number of plants and bacteria under drought or salt stress. Recently, a transgenic study has demonstrated that accumulation of the sugar alcohol mannitol in transgenic tobacco conferred protection against salt stress (Tarczynski et al., "Stress Protection of Transgenic Tobacco by Production of the Osmolyte Mannitol," Science, 259:508–510 (1993)). Two recent studies using a transgenic approach have demonstrated that metabolic engineering of the glycine betaine biosynthesis pathway is not only possible but also may eventually lead to production of stress-tolerant plants (Holmstrom et al., "Production of the Escherichia coli Betaine-Aldehyde Dehydrogenase, An Enzyme Required for the Synthesis of the Osmoprotectant Glycine Betaine, in Transgenic Plants," Plant J., 6:749–758 (1994); Rathinasabapathi et al., "Metabolic Engineering of Glycine Betaine Synthesis: Plant Betaine Aldehyde Dehydrogenases Lacking Typical Transit Peptides are Targeted to Tobacco Chloroplasts Where they Confer Betaine Aldehyde Resistance," Planta, 193:155–162 (1994)).

In addition to metabolic changes and accumulation of low molecular weight compounds, a large set of genes is transcriptionally activated which leads to accumulation of new proteins in vegetative tissue of plants under osmotic stress conditions, including the late embryogenesis abundant (LEA) family, dehydrines, and COR47 (Skriver et al., "Gene Expression in Response to Abscisic Acid and Osmotic Stress," Plant Cell, 2:503–512 (1990); Chandler et al., "Gene Expression Regulated by Abscisic Acid and its Relation to Stress Tolerance," Annu. Rev. Plant Physiol. Plant Mol. Biol., 45:113–141 (1994)). The expression levels of a number of genes have been reported to be correlated with desiccation, salt, or cold tolerance of different plant varieties of the same species. It is generally assumed that stress-induced proteins might play a role in tolerance, but the functions of many stress-responsive genes are unknown.

Elucidating the function of these stress-responsive genes and enzymes involved in the biosynthesis of stress-induced osmolytes will not only advance the understanding of plant adaptation and tolerance to environmental stresses, but also may provide important information for designing new strategies for crop improvement (Chandler et al., "Gene Expression Regulated by Abscisic Acid and its Relation to Stress Tolerance," Annu. Rev. Plant Physiol. Plant Mol. Biol., 45:113–141 (1994)).

In recent years, different stress-tolerant transgenic plants have been obtained (Tarczynski et al., "Stress Protection of Transgenic Tobacco by Production of Osmotic Mannitol," Science, 259:508–510 (1993); Shen et al., "Increased Resistance to Oxidative Stress in Transgenic Plants by Targeting Mannitol Biosynthesis to Chloroplasts," *Plant Physiol.*, 113: 1177–1183 (1997); Kishor et al., "Overexpression of Δ$^1$-pyrroline-5-carboxylate Synthetase Increases Proline Production and Confers Osmotolerance in Transgenic Plants," *Plant Physiol.*, 108:1387–1394 (1995); Pilon-Smits et al., "Improved Performance of Transgenic Fructan-Accumulating Tobacco Under Drought Stress," *Plant Physiol.*, 107: 125–130 (1995); Holmstrom et al., "Drought Tolerance on Tobacco," *Nature*, 379:683–684 (1996); Xu et al., "Expression of a Late Embryogenesis Abundant Protein Gene, HVA1, from Barley Confers Tolerance to Water Deficit and Salt Stress in Transgenic Rice," *Plant Physiol.*, 110:249–257 (1996); Nomura et al., *Synechococcus* sp. PPC 7942 Transformed with *E. coli* bet Genes Produces Glycine Betaine from Choline and Acquires Resistance to Salt Stress," *Plant Physiol.*, 107:703–708 (1995); Hayashi et al., "Transformation of *Arabidopsis thaliana* with codA Gene for Choline Oxidase: Accumulation of Glycine-Betaine and Enhanced Tolerance to Salt and Cold Stress," *Plant J.*, 12:133–142 (1997); Sheveleva et al., "Increased Salt and Drought Tolerance by D-ononitol Production in Transgenic *Nicotiana tabacum* L.," *Plant Physiol.*, 115:1211–1219 (1997)) by producing either a low molecular weight osmoprotectant (such as glycine betaine, mannitol, inositol, proline, fructan, trehalose, or D-ononitol) or a late embryogenesis abundant (LEA) protein. In transgenic tobacco transformed with the Δ$^1$-pyrroline-5-carboxylate synthetase cDNA (p5cs cDNA), it was found that proline accumulation was correlated with tolerance to drought and salinity stresses in plants. Overproduction of proline also enhanced root biomass and flower development in transgenic tobacco under drought-stress conditions (Kishor et al., "Overexpression of Δ$^1$-pyrroline-5-carboxylate Synthetase Increases Proline Production and Confers Osmotolerance in Transgenic Plants," *Plant Physiol.*, 108:1387–1394 (1995)). Proline is believed to be involved in osmotic adjustment, primarily as a cytoplasmic solute (Voetberg et al., "Growth of the Maize Primary Root at Low Water Potentials. III. Role of Increased Proline Deposition in Osmotic Adjustment," *Plant Physiol.*, 96:1125–1130 (1991)), as an osmoprotectant (Kishor et al., "Overexpression of Δ$^1$-pyrroline-5-carboxylate Synthetase Increases Proline Production and Confers Osmotolerance in Transgenic Plants," *Plant Physiol.*, 108:1387–1394 (1995)), and as a hydroxy radical scavenger (Smimoff et al., "Hydroxyl Radical Scavenging Activity of Compatible Solutes," *Phytochemistry*, 28:1057–1060 (1989)). Proline has also been reported to play a role in protecting enzymes from denaturation (Nikolopoulos et al., "Compatible Solutes and in vitro Stability of Salsola soda Enzymes: Proline Incompatibility," *Phytochemistry*, 30:411–413 (1991)) and stabilizing the machinery of protein synthesis (Kadpal et al., "Alterations in the Biosynthesis of Proteins and Nucleic Acids in Finger Millet (*Eleucine coracana*) Seedlings During Water Stress and the Effect of Proline on Protein Biosynthesis," *Plant Science*, 40:73–79 (1985)). Some or all of the presumed functions may contribute to osmotolerance of transgenic plants that overproduce proline. In most of the above-noted reports, tobacco (a dicot) was used as the model plant. Since dicots and monocots are quite different in their physiology, morphology, and, perhaps, response to abiotic stresses as well, it is important to study how overproduction of proline affects a major monocot cereal plant, such as rice, in response to stresses.

In addition, under normal environmental conditions, overproduction of the above-noted compounds or proteins will need extra energy and building blocks and may hamper the normal growth of plants. Thus, it is desirable to generate transgenic plants which synthesize a high level of an osmoprotectant or a protein only under stress conditions.

The phytohormone abscisic acid (ABA) is thought to mediate physiological processes in response to osmotic stress in plants (King, "Abscisic Acid in Developing Wheat Grains and its Relationship to Grain Growth and Maturation," *Planta*, 132:43–51(1976); Jones et al., "The Effect of Abscisic Acid on Cell Turgor Pressures, Solute Content, and Growth of Wheat Roots," *Planta*, 170:257–262 (1987)). Water stress by NaCl or dehydration can cause endogenous ABA levels to increase in plant tissues (Henson, "Effects of Atmospheric Humidity on Abscisic Acid Accumulation and Water in Leaves of Rice (*Oryza sativa* L.)," *Ann. Bot.*, 54:569–582 (1984); Jones et al., "The Effect of Abscisic Acid on Cell Turgor Pressures, Solute Content, and Growth of Wheat Roots," *Planta*, 170:257–262 (1987)). Mundy et al., "Abscisic Acid and Water-Stress Induce the Expression of a Novel Rice Gene," *The EMBO J.*, 7:2279–2286 (1988) found that ABA controls the accumulation of specific mRNAs and proteins both from developmental studies with seeds and physiological studies with water stressed tissues. Specific genes are expressed under stress conditions and can also be induced in unstressed tissues by the application of exogenous ABA (Singh et al., "Hormonal Regulation of Protein Synthesis Associated with Salt Tolerance in Plant Cell," *Proc. Natl. Acad. Sci. USA*, 84:739–743 (1987); Gomez et al., "A Gene Induced by the Plant Hormone Abscisic Acid in Response to Water Stress Encodes a Glycine-rich Protein," *Nature*, 334:262–264 (1988); Mundy et al., "Abscisic Acid and Water-Stress Induce the Expression of a Novel Rice Gene," *The EMBO J.*, 7:2279–2286 (1988); Chandler et al., "Gene Expression Regulated by Abscisic Acid and its Regulation to Stress Tolerance," *Annu. Rev. Plant Physiol.& Mol. Biol.* 45:113–114 (1994)).

In addition to the studies on the physiological roles of ABA, efforts are being made to investigate the molecular mechanism of ABA action, including the definition of ABA-response elements (ABREs) and the trans-acting factors that interact with ABREs. It was reported that a 75-bp fragment of the ABA-inducible wheat Em gene, when fused to a truncated CaMV 35S promoter, conferred a more than 10-fold ABA induction of GUS activity in rice protoplasts (Guiltinan et al., "A Plant Leucine Zipper Protein that Recognizes an Abscisic Acid Response Element," *Science*, 250:267–271 (1990)). Guiltinan et al. also found a leucine-zipper DNA binding protein, EmBP-1, which binds the ABRE sequence (CACGTGGC) in this 75-bp region. Transient assays in rice protoplasts revealed a 40-bp ABA-responsive fragment in the rice rab 16B promoter (Ono et al., "The rab 16B Promoter of Rice Contains Two Distinct Abscisic Acid-Responsive Elements," *Plant Physiol.*, 112: 483–491 (1996)). Two separate ABREs, motif I and motif III, are required for ABA induction; however, each can substitute for the other. The 40-bp-fragment-containing motif I fused to a truncated CaMV 35S promoter showed an approximate 4- to 5-fold induction by ABA (Ono et al., "The rab 16B Promoter of Rice Contains Two Distinct Abscisic Acid-Responsive Elements," *Plant Physiol.*, 112:483–491 (1996)). The ABREs are very similar to the G-box, which, as has been pointed out by Guiltinan et al., "A Plant Leucine Zipper Protein that Recognizes an Abscisic Acid Response Element," *Science*, 250:267–271 (1990), is present in some genes that are responsive to other environmental and physiological stimuli such as light (Giuliano et al., "An Evolutionarily Conserved Protein Binding Sequence Upstream of a Plant Light-Regulated Gene," *Proc. Natl. Acad. Sci. USA*, 85:7089–7093 (1988)) and auxin (Liu et al., "Soybean GH3 Promoter Contains Multiple Auxin-Inducible Elements," *Plant Cell*, 6:645–657 (1994)).

Studies on the promoter of the barley ABA-responsive HVA22 gene indicate that G-box sequences are necessary but not sufficient for ABA response (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995)). Instead, an ABA-responsive complex consisting of a G-box, namely, ABRE3, and a novel coupling element, CE1, is sufficient for high-level ABA induction. The results of linker-scan analyses and gain-of-function studies showed that the 49-bp ABA-response complex (ABRC 1) is the minimal sequence governing high-level ABA induction. A similar investigation on ABA induction of a barley late embryogenesis abundant (LEA) gene HVA1 (Shen et al., "Modular Nature of Abscisic Acid (ABA) Response Complexes: Composite Promoter Units that are Necessary and Sufficient for ABA Induction of Gene Expression in Barley," *The Plant Cell*, 8:1107–1119 (1996)) was conducted. Shen et al. found that the ABRC3 of this gene consists of a 10-bp element with an ACGT core (A2) and a sequence directly upstream, named CE3. Only one copy of this ABRC3 is sufficient to confer ABA induction when fused to a minimal promoter (Amy64). Thus, two types of ABRCs were reported by Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995) and Shen et al., "Modular Nature of Abscisic Acid (ABA) Response Complexes: Composite Promoter Units that are Necessary and Sufficient for ABA Induction of Gene Expression in Barley," *The Plant Cell*, 8:1107–1119 (1996), namely, ABRC1, consisting of ABRE3 and CE1 from HVA22 gene, and ABRC3, composed of CE3 and A2 from HVA1 gene.

The present invention is directed to producing transgenic cereal plants with improved water stress and salt stress tolerance.

SUMMARY OF THE INVENTION

The present invention relates to a method for conferring tolerance to salt stress and drought stress in a monocot plant including transforming the monocot plant with an expression cassette comprising at least one ABRC unit, a minimal promoter, and a DNA molecule that increases tolerance to salt stress and drought stress in plants, wherein the at least one ABRC unit, the minimal promoter, and a DNA molecule are operably linked together to permit expression of the DNA molecule.

The present invention also relates to a transgenic monocot plant transformed with a DNA molecule that increases tolerance to salt stress and drought stress operably linked to at least one ABRC unit and a minimal promoter.

The present invention allows the production of cereal plants with increased tolerance to water stress (drought) and salt stress. In particular, a salt- and drought-stress-inducible promoter can be used to create transgenic cereal plants with higher levels of biomass under stress conditions, when compared to the use of a constitutive promoter.

Leaves: 0.02±0.01(L1), 1±0.3 (L2), 7±2 (L5); 0.02±0.01 (L3), 14±4 (L7), 12±3 (L11); 0.02±0.01 (NT).

Roots: 0.01±0.01(L1), 0.8±0.2(L2), 6±1(L5); 0.01±0.01 (L3), 9±2(L7), 7±2(L11); 0.01±0.01 (NT).

Data represent the average results of four experiments by using different tillers of the same $R_0$ line. Bar represents the SE 4-MU, 4-methylumbelliferone.

Figure 9:
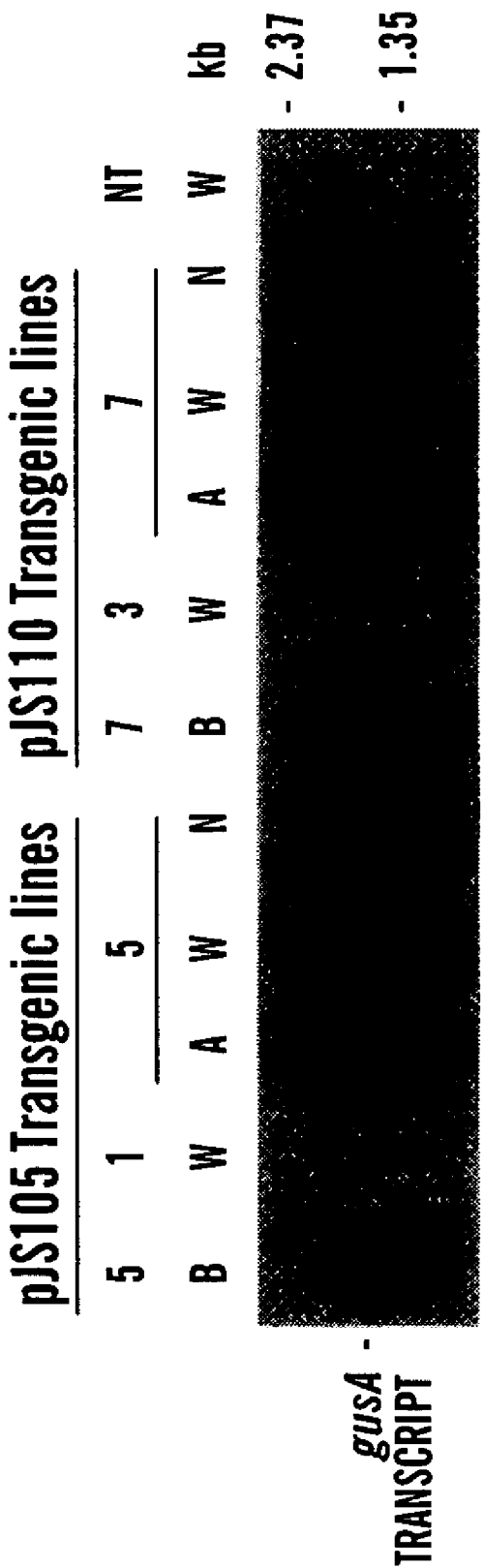

FIG. 9 shows ABA-, water deficit-, and NaCl-induced gusA expression confirmed by Northern hybridization analysis. Five µg of total RNA were fractionated in a 1% formaldehyde agarose gel and blotted onto a nylon membrane hybridized with [α-$^{32}$P]dCTP-labeled gusA coding sequence. Equal loading of the RNA samples was confirmed by ethidium bromide staining of rRNA in a parallel-running gel. Molecular sizes (kb) of two fragments from RNA ladder (GIBCO BRL, Life Technology, Inc., Rockville, Md.) are indicated on the right side. A=ABA: 50 µM for 20 hours; B=basal level without any treatment; W=water deficit: water withheld for 6 days; N=NaCl: 150 mM NaCl, for 72 hours.

Figure 10A:
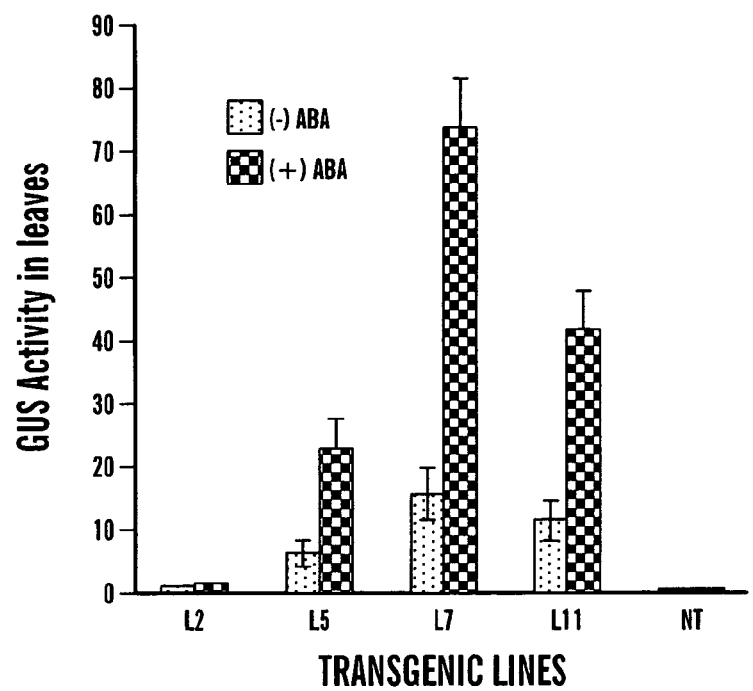
Figure 10B:
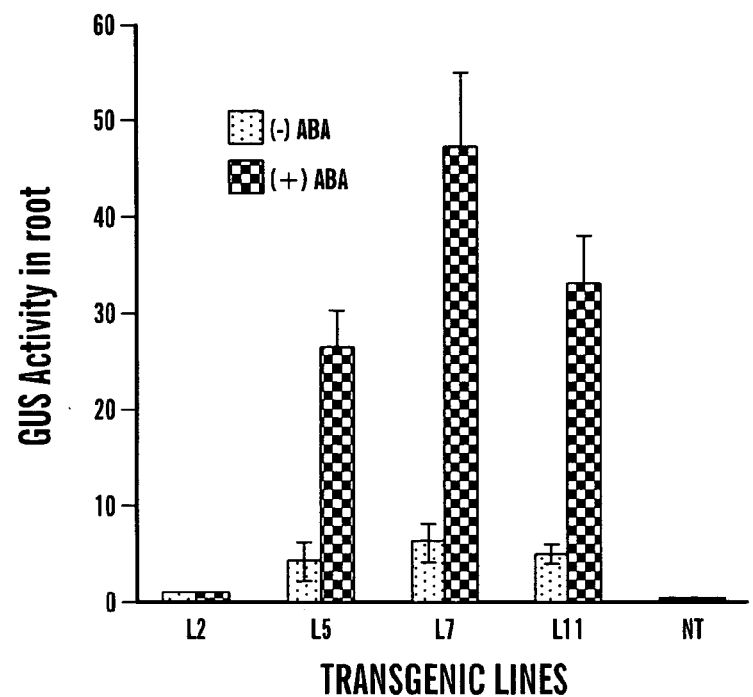

FIGS. 10A and 10B show ABA-induced GUS activity (4-MU nmol h$^{-1}$ mg protein$^{-1}$) in 2-week-old R$_1$ seedlings of transgenic plants. All data were derived from the results of eight seedlings. pJS105 (one copy of ABRC1): L2 and L5; pJS110 (four copies of ABRC1): L7 and L11. NT=non-transgenic plants. x indicates the induction fold. Bar represents the SE. FIG. 10A-Leaves: Mean± SE values of ABA-induced GUS activity are: L2, 1±0.2 (−ABA), 1.2±0.3 (+ABA), 1.2x; L5, 6±2 (−ABA), 22±5 (+ABA), 4x; L7, 15±4 (−ABA), 73±8 (+ABA), 5x; L11, 11±3 (−ABA), 41x; ±6 (+ABA), 4x; NT, 0.02±0.01 (−ABA), 0.02±0.01 (+ABA), 1x. FIG. 10B-Roots: Mean±SE values of ABA-induced GUS activity are: L2, 0.8±0.2 (−ABA), 0.9±0.2 (+ABA), 1x; L5, 4±2 (−ABA), 26±5 (+ABA), 7x; L7, 6±2 (−ABA), 48±10 (+ABA), 8x; L11, 5±1 (−ABA), 33±5 (+ABA), 7x; NT, 0.01±0.01 (−ABA), 0.01±0.01 (+ABA), 1x.

DETAILED DESCRIPTION OF THE INVENTION

The present invention relates to a method for conferring tolerance to salt stress and drought stress in a monocot plant including transforming the monocot plant with an expression cassette comprising at least one ABRC unit, a minimal promoter, and a DNA molecule that increases tolerance to salt stress and drought stress in plants, wherein the at least one ABRC unit, the minimal promoter, and a DNA molecule are operably linked together to permit expression of the DNA molecule.

Monocot plants which can be transformed in accordance with the subject invention are members of the family Gramineae (also known as Poaceae), and include rice (genus *Oryza*), wheat, maize (corn), barley, oat, rye, millet, and sorghum. Preferably, the cereal is rice, wheat, or corn, and most preferably the cereal is rice. Many species of cereals can be transformed, and, within each species, there are numerous subspecies and varieties that can be transformed. For example, within the rice species is subspecies Indica rice (*Oryza sativa* ssp. Indica), which includes the varieties IR36, IR64, IR72, Pokkali, Nona Bokra, KDML105, Suponburi 60, Suponburi 90, Basmati 385, and Pusa Basmati 1. Another rice subspecies *is* Japonica, which includes Nipponbere, Kenfeng and Tainung 67. Examples of suitable maize varieties include A188, B73, VA22, L6, L9, K1, 509, 5922, 482, HNP, and IGES. Examples of suitable wheat varieties include Pavon, Anza, Chris, Coker 983, FLA301, FLA302, Fremont and Hunter.

Having identified the monocot plant of interest, plant cells suitable for transformation include mature embryos, immature embryos, calli, suspension cells, and protoplasts. It is particularly preferred to use mature embryos and immature embryos.

In a preferred embodiment, the at least one ABRC unit is from a barley HVA22 gene or a barley HVA1 gene. The sequence for the at least one ABRC unit from a barley HVA22 gene, a 49-bp ABA-responsive complex, is set forth in Shen et al., "Functional Dissection of an Abscisic Acid (ABA)-Inducible Gene Reveals Two Independent ABA-Responsive Complexes Each Containing a G-Box and Novel cis-Acting Element," *The Plant Cell,* 7:295–307 (1995), which is hereby incorporated by reference. The sequence for the ABRC unit from a barley HJVA1 gene is set forth in Shen et al., "Modular Nature of Abscisic Acid (ABA) Response Complexes: Composite Promoter Units that are Necessary and Sufficient for ABA Induction of Gene Expression in Barley," *The Plant Cell,* 8:1107–1119 (1996). In a most preferred embodiment, up to four of the ABRC units are operably linked together in the expression cassette.

Suitable DNA molecules that increase tolerance to salt stress and drought stress in plants include a Δ$^1$-pyrroline-5-carboxylate synthetase gene (P5CS), a feedback-inhibition insensitive mutant, P5CS-129A, of the P5CS gene, VA1, COR47, a mannitol 1-P-dehydrogenase gene, a gene for the biosynthesis of polyamines, a gene for the biosynthesis of glycine betaine, trehalose, D-ononitol or fructans, and a gene for regulating the expression of stress-responsive genes. In a preferred embodiment, the DNA molecule that increases tolerance to salt stress and drought stress in plants is the P5CS gene of mothbean. The sequence of the P5CS gene can be found in Kishor et al., "Overexpression of Δ$^1$-pyrroline-5-carboxylate Synthetase Increases Proline Production and Confers Osmotolerance in Transgenic Plants," *Plant Physiol.,* 108:1387–1394 (1995), which is hereby incorporated by reference, and the sequence of the PSCS-129A mutant gene can be found in Zhang et al., "Removal of Feedback Inhibition of P5CS in Plants," *J. Biol. Chem.,* 270:20491–20496 (1995), which is hereby incorporated by reference. The sequence of the Hva1 gene can be found in Hong et al., "Cloning and Characterization of a cDNA Encoding a mRNA Rapidly Induced by ASA in Barley Aleurone Layers," *Plant Mol. Biol.,* 11:495–506 (1988), which is hereby incorporated by reference.

Suitable minimal promoters include Act1-100 of rice, a shortened α-amylase promoter of barley or rice, a shortened maize ubiquitin promoter, or a shortened CaMV 35S promoter. In a preferred embodiment, the minimal promoter is Act1-100 of rice.

In a preferred embodiment, the expression cassette comprising the at least one ABRC unit, the minimal promoter, and the DNA molecule that increases tolerance to salt stress and drought stress in plants is salt stress or drought stress inducible.

These monocot plant cells are transformed with a DNA molecule, which could be RNA or DNA and which is preferably cDNA, encoding a molecule that increases tolerance to salt stress and drought stress in plants. The DNA molecule can be biologically isolated or synthetic. In the following Examples, a key enzyme for proline biosynthesis, Δ$^1$-pyrroline-5-carboxylate synthase (P5CS), is encoded by the P5CS gene of mothbean. However, other genes encoding a molecule that increases tolerance to salt stress and drought stress in plants can also be utilized.

Transformation of plant cells can be accomplished by using a plasmid. The plasmid is used to introduce the DNA molecule that increases tolerance to salt stress and drought stress in plants into the plant cell. Accordingly, a plasmid preferably includes a DNA molecule that increases tolerance to salt stress and drought stress in plants inserted into a unique restriction endonuclease cleavage site. Heterologous DNA, as used herein, refers to DNA not normally present in the particular host cell transformed by the plasmid. DNA is inserted into the vector using standard cloning procedures readily known in the art. This generally involves the use of restriction enzymes and DNA ligases, as described by Sambrook et al., *Molecular Cloning: A Laboratory Manual,* 2d edition, Cold Spring Harbor Laboratory Press, Cold Spring Harbor, N.Y. (1989), which is hereby incorporated by reference. The resulting plasmid which includes a DNA molecule that increases tolerance to salt stress and drought stress in plants can then be used to transform a host cell, such as an *Agrobacterium* and/or a plant cell. (See generally, *Plant Molecular Biology Manual*, 2nd Edition, Gelvin et al., Eds., Kluwer Academic Press, Dordrecht, Netherlands (1994), which is hereby incorporated by reference).

For plant transformation, the plasmid preferably also includes a selectable marker for plant transformation. Commonly used plant selectable markers include the hygromycin phosphotransferase (hpt) gene, the phosphinothricin acetyl transferase gene (bar), the 5-enolpyruvylshikimate-3-phosphate synthase gene (EPSPS), neomycin 3'-O-phosphotransferase gene (npt II), or acetolactate synthase gene (ALS). Information on these selectable markers can be found in Bowen, "Markers for Plant Gene Transfer" in *Transgenic Plants*, Kung et al., Eds., Vol. 1, pp. 89–123, Academic Press, NY (1993), which is hereby incorporated by reference.

In a preferred embodiment, the plasmid is designated pJS112, pJP21, or pJPM001.

The plasmid designated pJS112 has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209, under ATCC Accession No. PTA-309 on Jun. 17, 1999.

The plasmid designated pJP21 has been deposited pursuant to, and in satisfaction of, the requirements of the Budapest Treaty on the International Recognition of The Deposit of Microorganisms for The Purposes of Patent Procedure, with the American Type Culture Collection (ATCC), 10801 University Boulevard, Manassas, Va. 20110-2209, under ATCC Accession No. PTA-3928 on Jan. 3, 2002.

The plasmid designated pJPM001 has been deposited pursuant to, and in satisfaction of, the requirements of the Budapest Treaty on the International Recognition of The Deposit of Microorganisms for The Purposes of Patent Procedure, with the American Type Culture Collection (ATCC), 10801 University Boulevard, Manassas, Va. 20110-2209, under ATCC Accession No. PTA-3929 on Jan. 3, 2002.

For plant transformation, the plasmid also preferably includes a nucleic acid molecule encoding a 3' terminator such as that from the 3' non-coding region of genes encoding a proteinase inhibitor, actin 1, or nopaline synthase (nos).

Other suitable plasmids for use in the subject invention can be constructed. For example, genes encoding a DNA molecule that increases tolerance to salt stress and drought stress in plants other than the P5CS gene of mothbean could be ligated into plasmid JS 112 after use of restriction enzymes to remove the P5CS gene. Other minimal promoters could replace the rice actin 1 gene promoter present in plasmid JS 112. Alternatively, other plasmids in general containing genes encoding a DNA molecule that increases tolerance to salt stress and drought stress in plants under the control of a suitable minimal promoter, with suitable selectable markers, can be readily constructed using techniques well known in the art.

Having identified the plasmid, one technique of transforming cereal plant cells with a DNA molecule that increases tolerance to salt stress and drought stress in plants is by contacting the plant cell with an inoculum of an *Agrobacterium* bacteria transformed with the plasmid comprising the DNA molecule that increases tolerance to salt stress and drought stress in plants. Generally, this procedure involves inoculating the plant cells with a suspension of the transformed bacteria and incubating the cells for 48 to 72 hours on regeneration medium without antibiotics at 25–28° C.

Bacteria from the genus *Agrobacterium* can be utilized to transform plant cells. Suitable species include *Agrobacterium tumefaciens* and *Agrobacterium rhizogenes*. *Agrobacterium tumefaciens* (e.g., strains LBA4404 or EHA105) is particularly useful due to its well-known ability to transform plants.

In inoculating the cells of monocot plants with *Agrobacterium* according to the subject invention, the bacteria must be transformed with a vector which includes a gene encoding for an enzyme for proline biosynthesis.

Plasmids, suitable for incorporation in *Agrobacterium*, which include a DNA molecule that increases tolerance to salt stress and drought stress in plants, contain an origin of replication for replication in the bacterium *Escherichia coli*, an origin of replication for replication in the bacterium *Agrobacterium tumefaciens*, T-DNA right border sequences for transfer of genes to plants, and marker genes for selection of transformed plant cells. Particularly preferred is the vector pBI121 which contains a low-copy RK2 origin of replication, the neomycin phosphotransferase (nptII) marker gene with a nopaline synthase (NOS) promoter and a NOS 3' polyadenylation signal. T-DNA plasmid vector pBI121 is available from Clonetech Laboratories, Inc., 4030 Fabian Way, Palo Alto, Calif. 94303. A DNA molecule that increases tolerance to salt stress and drought stress in plants is inserted into the vector to replace the beta-glucuronidase (GUS) gene.

Typically, *Agrobacterium* spp. are transformed with a plasmid by direct uptake of plasmid DNA after chemical and heat treatment, as described by Holsters et al. "Transfection and Transformation of *Agrobacterium tumefaciens*," *Mol. Gen. Genet.*, 163:181–187 (1978), which is hereby incorporated by reference; by direct uptake of plasmid DNA after electroporation, as described by Shen et al., "Efficient Transformation of *Agrobacterium* spp. by High Voltage Electroporation," *Nucleic Acids Research*, 17:8385 (1989), which is hereby incorporated by reference; by triparental conjugational transfer of plasmids from *Escherichia coli* to *Agrobacterium* mediated by a Tra+help strain as described by Ditta et al., "Broad Host Range DNA Cloning System for Gram-negative Bacteria: Construction of a Gene Bank of *Rhizobium meliloti*," Proc. Natl. Acad. Sci. USA, 77:7347–7351 (1981), which is hereby incorporated by reference; or by direct conjugational transfer from *Escherichia coli* to *Agrobacterium* as described by Simon et al., "A Broad Host Range Mobilization System for in vivo Genetic Engineering: Transposon Mutagenesis in Gram-Negative Bacteria," *Biotechnology*, 1:784–791 (1982), which is hereby incorporated by reference.

Another method for introduction of a plasmid containing nucleic acid encoding an enzyme for proline biosynthesis into a plant cell is by transformation of the plant cell nucleus, such as by particle bombardment. As used throughout this application, particle bombardment (also known as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the heterologous DNA. Alternatively, the target cell can be surrounded by the plasmid so that the plasmid is carried into the cell by the wake of the particle. Biologically active particles (e.g., dried bacterial cells containing the plasmid and heterologous DNA) can also be propelled into plant cells.

A further method for introduction of the plasmid into a plant cell is by transformation of plant cell protoplasts (stable or transient). Plant protoplasts are enclosed only by a plasma membrane and will therefore take up macromolecules like heterologous DNA. These engineered protoplasts can be capable of regenerating whole plants. Suitable methods for introducing heterologous DNA into plant cell protoplasts include electroporation and polyethylene glycol (PEG) transformation. As used throughout this application, electroporation is a transformation method in which, generally, a high concentration of plasmid DNA (containing heterologous DNA) is added to a suspension of host cell protoplasts and the mixture shocked with an electrical field of 200 to 600 V/cm. Following electroporation, transformed cells are identified by growth on appropriate medium containing a selective agent.

As used throughout this application, transformation encompasses stable transformation in which the plasmid is integrated into the plant chromosomes.

In the Examples which follow, rice has been transformed using biolistic transformation. Other methods of transformation have also been used to successfully transform rice plants, including the protoplast method (for a review, see Cao et al., "Regeneration of Herbicide Resistant Transgenic Rice Plants Following Microprojectile-Mediated Transformation of Suspension Culture Cells," *Plant Cell Rep.,* 11:586–591 (1992), which is hereby incorporated by reference), and the *Agrobacterium* method (Hiei et al., "Efficient Transformation of Rice (*Oryza sativa* L.) Mediated by *Agrobacterium* and Sequence Analysis of the Boundaries of the T-DNA," *The Plant Journal,* 6:271–282 (1994), which is hereby incorporated by reference). Biolistic transformation has also been used to successfully transform maize (for a review, see Mackey et al., "Transgenic Maize," In *Transgenic Plants*, Kung et al., Eds., vol. 2, pp. 21–33 (1993), which is hereby incorporated by reference) and wheat (see U.S. Pat. No. 5,405,765 to Vasil et al., which is hereby incorporated by reference).

Once a monocot plant cell or protoplast is transformed in accordance with the present invention, it is regenerated to form a transgenic monocot plant. Generally, regeneration is accomplished by culturing transformed cells or protoplasts on medium containing the appropriate growth regulators and nutrients to allow for the initiation of shoot meristems. Appropriate antibiotics are added to the regeneration medium to inhibit the growth of *Agrobacterium* or other contaminants and to select for the development of transformed cells or protoplasts. Following shoot initiation, shoots are allowed to develop in tissue culture and are screened for marker gene activity.

In suitable transformation methods, the monocot plant cell to be transformed can be in vitro or in vivo, i.e. the monocot plant cell can be located in a monocot plant.

The present invention also relates to a transgenic monocot plant transformed with a DNA molecule that increases tolerance to salt stress and drought stress operably linked to at least one ABRC unit and a minimal promoter.

The invention also provides seed produced by the transgenic monocot plant. The invention is also directed to seed, which upon germination, produces the transgenic monocot plant.

Also encompassed by the present invention are transgenic monocot plants transformed with fragments of the DNA molecules that increase tolerance to salt stress and drought stress of the present invention. Suitable fragments capable of conferring water stress or salt stress tolerance to monocot plants can be constructed by using appropriate restriction sites. A fragment refers to a continuous portion of the DNA molecule that increases tolerance to salt stress and drought stress that is less than the entire molecule.

Non-essential nucleotides could be placed at the 5' and/or 3' ends of the fragments (or the full length DNA molecules that increase tolerance to salt stress and drought stress) without affecting the functional properties of the fragment or molecule (i.e. in increasing water stress or salt stress tolerance). For example, the DNA molecule that increases tolerance to salt stress and drought stress may be conjugated to a signal (or leader) sequence at the N-terminal end (for example) of the DNA molecule that increases tolerance to salt stress and drought stress which co-translationally or post-translationally directs transfer of the DNA molecule that increases tolerance to salt stress and drought stress. The nucleotide sequence may also be altered so that the DNA molecule that increases tolerance to salt stress and drought stress is conjugated to a linker or other sequence for ease of synthesis, purification, or identification.

The transgenic cereal plant cell or protoplast or plant can also be transformed with a nucleic acid encoding a selectable marker, such as the bar gene, to allow for detection of transformants, and with a nucleic acid encoding the cauliflower mosaic virus 35S promoter to control expression of the bar gene. Other selectable markers include genes encoding EPSPS, nptII, or ALS. Other promoters include those from genes encoding actin 1, ubiquitin, and PINII. These additional nucleic acid sequences can also be provided by the plasmid encoding a gene that imparts tolerance to salt stress and drought stress and its promoter. Where appropriate, the various nucleic acids could also be provided by transformation with multiple plasmids.

While the DNA molecule that increases tolerance to salt stress and drought stress referred to herein encodes, for example, a gene that impart tolerance to salt stress and drought stress, nucleotide identity to previously sequenced salt stress and drought stress genes is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the salt stress and drought stress gene nucleotide and/or amino acid sequences which have minimal influence on the properties, secondary structure, and hydrophilic/hydrophobic nature of the encoded salt stress and drought stress gene. These variants are encompassed by the present invention.

EXAMPLES

Example 1

Plasmid Construction for Rice Transformation

Figure 1:
FIG. 1 shows a schematic diagram of plasmids pJS102, pJS102, pJS110, pJP21, and pJPM001. Each plasmid consists of two gene expression cassettes. The p5cs cDNA is regulated by either the Act1 promoter or an ABA-inducible promoter complex (AIPC), and the potato Pin2 3' region was used as the terminator. In the bar cassette, the bar gene is driven by the CaMV 35S promoter. Only BamHI restriction sites, used for DNA digestion in DNA blot hybridization, are indicated. Plasmid pJS110 is identical to pJS112 except that the p5cs is replaced by uidA.

Three plasmids were constructed (See FIG. 1). The first plasmid had a constitutive promoter, the rice actin 1 gene promoter (Act1), to drive the expression of p5cs (referred to as Act1-p5cs). A 2.4-kb SalI fragment containing the mothbean p5cs cDNA (Hu et al., "A Bifunctional Enzyme ($\Delta^1$-pyrroline-5-carboxylate synthetase) Catalyzes the First Two Steps in Proline Biosynthesis in Plants," *Proc. Natl. Acad. Sci. USA,* 89:9354–9358 (1992), which is hereby incorporated by reference) was isolated from the plasmid pUbiP5CS, and this fragment was blunted with Klenow DNA polymerase and subcloned into the SmaI site of the pBY505 expression vector (Wang et al., "A Vector for Inserting Foreign Genes and Selection of Transformed Rice Plants," *Rice Biotech. Quarterly*, 22:8 (1995), which is hereby incorporated by reference) to create pJS102 (pJS102: Rice actin 1 promoter/P5CS cDNA/Pin 2 3'//35S promoter/ bar/Nos 3'). The second plasmid had an ABA-inducible promoter (Su et al., "Dehydration-stress Regulated Transgene Expression in Stably Transformed Rice Plants," *Plant Physiol.*, 117:913–922 (1998), which is hereby incorporated by reference). It was constructed by inserting the 2.4-kb p5cs fragment into the SmaI site of an expression vector, pJS109 (Su et al., "Dehydration-stress Regulated Transgene Expression in Stably Transformed Rice Plants," *Plant Physiol.*, 117:913–922 (1998), which is hereby incorporated by reference), to create plasmid pJS112 (pJS112: ABRC4/Act1-100 promoter/Hva22 intron/P5CS cDNA/Pin2 3'//35S promoter/bar/Nos 3'). A third plasmid, pJS110, was identical to pJS112 except that the p5cs fragment is replaced by uidA.

Example 2

Production of Transgenic Rice Plants

Calli were induced in LS medium (Cao et al., "Assessment of Rice Genetic Transformation Techniques," in *Rice Biotechnology*, Toenniessen et al., eds, CAB International, Oxon, UK, pp 175–198 (1991), which is hereby incorporated by reference) from mature rice embryos (*Oryza sativa* L. cv. Kenfong), and suspension cultures were initiated from embryogenic calli in liquid AA medium (Cao et al., "Assessment of Rice Genetic Transformation Techniques," in *Rice Biotechnology*, Toenniessen et al., eds, CAB International, Oxon, UK, pp 175–198 (1991), which is hereby incorporated by reference). Fine suspension cells (subcultured for 3 days prior to bombardment) were bombarded with tungsten particles coated with one of the three plasmids, according to the procedure described by Cao et al. (Cao et al, "Regeneration of Herbicide Resistant Transgenic Rice Plants Following Microprojectile-mediated Transformation of Suspension Culture Cells," *Plant Cell Reports*, 11:586–591 (1992), which is hereby incorporated by reference). Resistant calli were selected in KPR medium (Cao et al., "Assessment of Rice Genetic Transformation Techniques," in *Rice Biotechnology*, Toenniessen et al., eds, CAB International, Oxon, UK, pp 175–198 (1991), which is hereby incorporated by reference) supplemented with 8 mg/L Bialaphos as selective agent for 6 weeks (subcultured every two weeks). The resistant calli were transferred to MS regeneration medium (Cao et al, "Regeneration of Herbicide Resistant Transgenic Rice Plants Following Microprojectile-mediated Transformation of Suspension Culture Cells," *Plant Cell Reports*, 11:586–591 (1992), which is hereby incorporated by reference) containing 3 mg/L Bialaphos to regenerate into plants. Regenerated plants were transplanted into sterilized soil and grown in the greenhouse (30° C. day/20° C. night with supplemental light for 10 hours). The presence of the transgenes in regenerated rice plants was detected by an herbicide-resistance test (Cao et al, "Regeneration of Herbicide Resistant Transgenic Rice Plants Following Microprojectile-mediated Transformation of Suspension Culture Cells," *Plant Cell Reports*, 11:586–591 (1992), which is hereby incorporated by reference).

Example 3

DNA and RNA Blot Hybridization Analysis of Transgenic Rice Plants

For Southern blot analysis (See FIG. 2), genomic DNA from transgenic rice plants was carried out using 8 µg total DNA as previously described (Cao et al, "Regeneration of Herbicide Resistant Transgenic Rice Plants Following Microprojectile-mediated Transformation of Suspension Culture Cells," *Plant Cell Reports*, 11:586–591 (1992), which is hereby incorporated by reference). Genomic DNA was digested with BamHI and separated in a 0.8% agarose gel. A DIG-labeled 2.4-kb p5cs coding sequence was used as a probe. For RNA blot hybridization analysis (See FIG. 3), total RNA from $R_2$ leaves of transgenic rice plants was isolated as described (Hihara et al., "Isolation and Characterization of Two cDNA Clones for mRNA That are Abundantly Expressed in Immature Anthers of Rice (*Oryza sativa* L.)," *Plant Mol. Biol.*, 30:1181–1193 (1996), which is hereby incorporated by reference). 20 µg of total RNA from the transgenic rice was subjected to electrophoresis in a 1.0% formaldehyde agarose gel. After electrophoresis, RNA was transferred to a nylon membrane (Boehringer Mannheim, Indianapolis, Ind.). The 2.4-kb P5CS coding region was used as a probe and labeled with $\alpha$-$^{32}$P-dCTP by using Random Primers DNA Labeling Kit. Gel preparation, hybridization and washing were carried out as described by Sambrook et al., *Molecular Cloning: A Laboratory Manual*, $2^{nd}$ Ed., Cold Spring Harbor Laboratory, Cold Spring Harbor, N.Y. (1989), which is hereby incorporated by reference.

Example 4

Test for Growth Performance of $R_2$ Seedlings Under Stress Conditions

Stress treatments for $R_2$ seedlings included dehydration with PEG 8000 and NaCl. The $R_2$ seeds from the p5cs transgenic and control uidA transgenic plants, and transformation procedure-derived nontransgenic (NT) plants, were surface-sterilized. The seeds were placed on 10% PEG 8000-containing half-strength (½) MS medium in Magenta boxes and cultured in a growth room (25° C.) for 3 days in the dark and then under light for an additional 11 days. For NaCl stress, the sterilized $R_2$ seeds were first cultured in ½ MS medium containing 200 mM NaCl, and placed in the dark for 4 days. The germinated seeds were grown in the growth room (25° C. with 10 hours of photoperiod) for an additional 10 days. The 14-day-old seedlings were transferred to ½ MS medium containing 100 mM NaCl and cultured for 4 more days. Then, the 18-day-old seedlings were grown in ½ MS medium containing 200 mM NaCl in the growth room for another 10 days. The 2-week-old PEG-stressed plants and the 4-week-old NaCl-stressed plants were used for shoot-weight and root-weight measurements.

Example 5

Determination of Free Proline Content

Leaves of transgenic plants ($R_2$) were used for proline analysis. For water stress, water was withheld from 3-month-old transgenic plants for 5 or 8 days in the greenhouse. To start salinity stress, 200 mM NaCl solution was used to water the transgenic plants for 2 or 3 days. Additional NaCl solution was applied to the plants each day thereafter to create a stable soil salinity condition. A uidA-transgenic line (Su et al., "Dehydration-stress Regulated Transgene Expression in Stably Transformed Rice Plants," *Plant Physiol.*, 117:913–922 (1998), which is hereby incorporated by reference) with Basta resistance and very low GUS activity ($\leq 0.01$ nmol/h/mg protein) served as a control for endogenous proline content. Leaves (0.25 g) from both the non-stressed and stressed plants were collected at different timepoints and extracted with 5 ml of 3% sulfosalicylic acid. The filtered extract was used for determination of proline content as described by Bates et al., "Rapid Determination of Free Proline for Water-Stress Studies," *Plant and Soil*, 39:205–207 (1973), which is hereby incorporated by reference. As the proline content varies from leaf to leaf and also with the age of the plants, leaves with the same age and size were used.

Example 6

Growth and Stress Treatments of Plants in Soil

Refined and sterilized field soil was used to grow the rice plants in the greenhouse. $R_2$ seeds were germinated in ½ MS medium for 7 days, and the 7-day-old seedlings were transplanted into soil in small pots (8×8 inches) with holes in the bottom (4 to 6 plants per pot). The pots were kept in flat-bottomed trays containing water. The seedlings were grown for an additional 2 weeks, and, within the third week, they were tested for Basta resistance. Two Basta-resistant plants with the same plant height per pot were selected for stress treatments. Stress treatments were carried out essentially as described by Xu et al., "Expression of a Late Embryogenesis Abundant Protein Gene, HVA1, From Barley Confers Tolerance To Water Deficit and Salt Stress in Transgenic Rice," *Plant Physiol.*, 110:249–257 (1996), which is hereby incorporated by reference. In the first round of stress treatment, water was withheld from the trays for 7 days, and then the stressed plants were resupplied with water for 2 days. One or three additional rounds of stress treatments were imposed on the plants. For salt stress, 3-week-old plants were transferred to trays containing 300 mM NaCl solution for 20 days. The NaCl solution was changed every 3 days to maintain a constant concentration of NaCl in the soil. The pots containing stressed plants were transferred back to trays containing tap water to allow the stressed plants to recover and grow without stress for 10 days. After the 10 days of recovery, a second round of salt stress was imposed by using the same concentration of NaCl solution for 10 days. Liquid fertilizer (N:P:K=15:5:15) mixed with tap water or NaCl solution was applied to the plants weekly.

Example 7

Production of Transgenic Plants and Southern Blot Hybridization Analysis

To test the stress-inducible expression of p5cs cDNA in transgenic plants, three plasmids were constructed as shown in FIG. 1. pJS102 contained a constitutive expression promoter (rice Act1), and pJS112 contained an ABA-inducible promoter, the ABA-inducible promoter complex (AIPC). The stress-inducible expression of AIPC-directed transgene expression was confirmed by a GUS activity assay (Su et al., "Dehydration-stress Regulated Transgene Expression in Stably Transformed Rice Plants," *Plant Physiol.*, 117:913–922 (1998), which is hereby incorporated by reference); thus the AIPC is referred to as a stress-inducible promoter complex (SIPC) in the following text. The SIPC used in the present experiment contained 4-copies of ABRC 1 from the barley HVA22 gene, the rice Act1 minimal promoter (180 bp), and the HVA22 intron. pJS110 was also used as a control because it contained the same components as pJS112 except that the reporter gene was uidA. All three plasmids contained a bacterial phosphinothricin acetyltransferase gene (bar) driven by the CaMV 35S promoter for selection. These three plasmids were used to transform rice suspension cells. After transformation of rice, the Bialaphos-resistant calli were transferred to MS regeneration medium and regenerated into plants.

Figure 2:
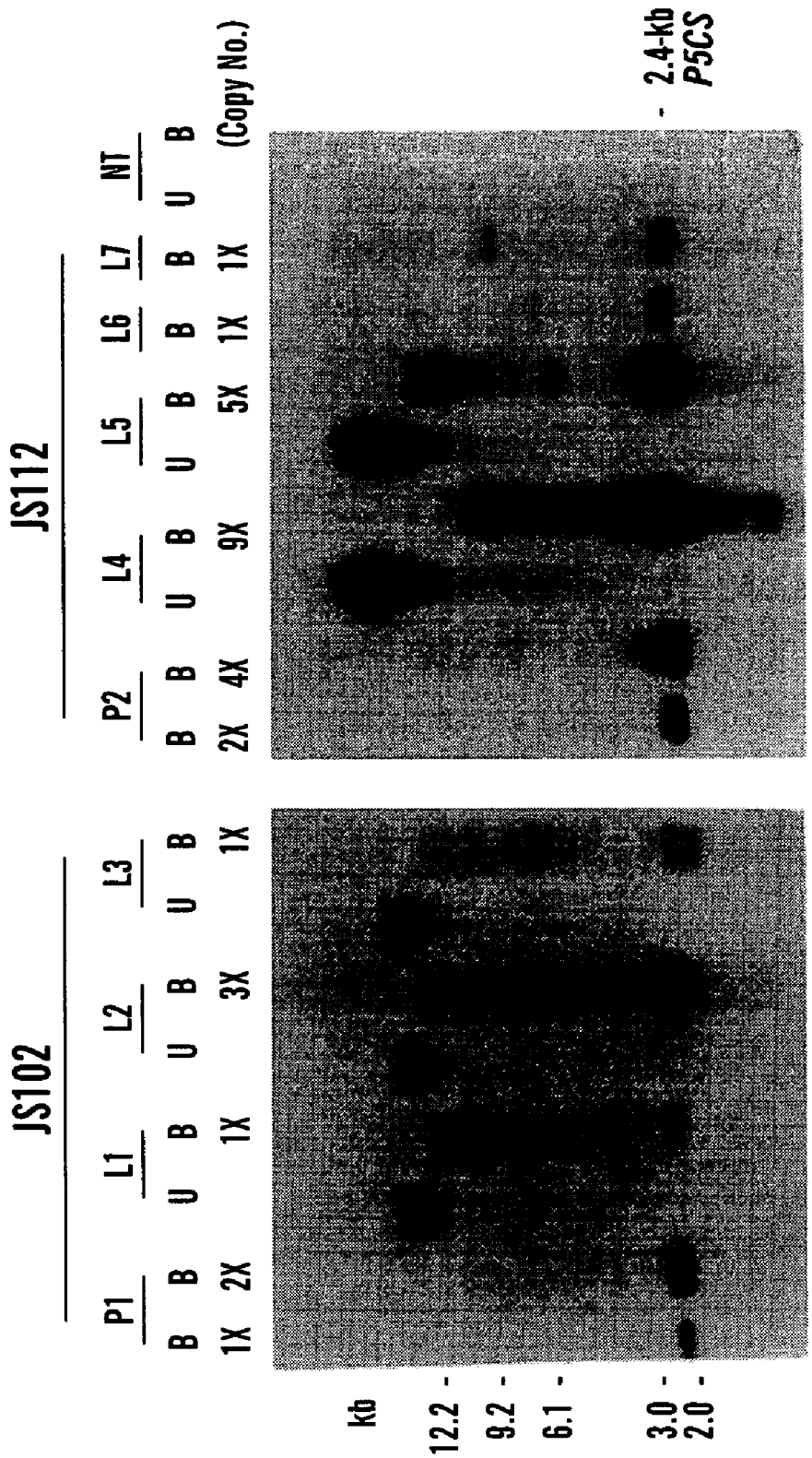
FIG. 2 shows Southern Blot Hybridization patterns of p5cs transgenes in the transgenic rice plants. Molecular sizes of 1-kb DNA ladder (GIBCO BRL, Life Technology, Inc., Rockville, Md.) are indicated on the left side. P1=plasmid pJS102; P2=plasmid pJS112; U=undigested sample; B=BamHI-digested sample. Copy numbers (X) of the transgenes were estimated by densitometry.

After Basta resistance analysis, Southern blot hybridization was carried out. Results in FIG. 2 showed that all 7 transgenic lines ($R_0$) contained the expected 2.4-kb hybridization band, although several of these lines also contained additional hybridization bands of varying sizes that may represent rearranged or methylated copies of the p5cs-containing DNA fragment. Transgene copy number was estimated by comparing the intensity of hybridization bands of BamHI-digested genomic DNA from transgenic plants to the bands of known quantities of plasmid DNA (P1 and P2). The copy number of the transgene, including rearranged copies, varied between 1 and 9.

Example 8

Water- and Salt-Stress-Induced p5cs mRNA Synthesis in Transgenic Rice Plants

Figure 3:
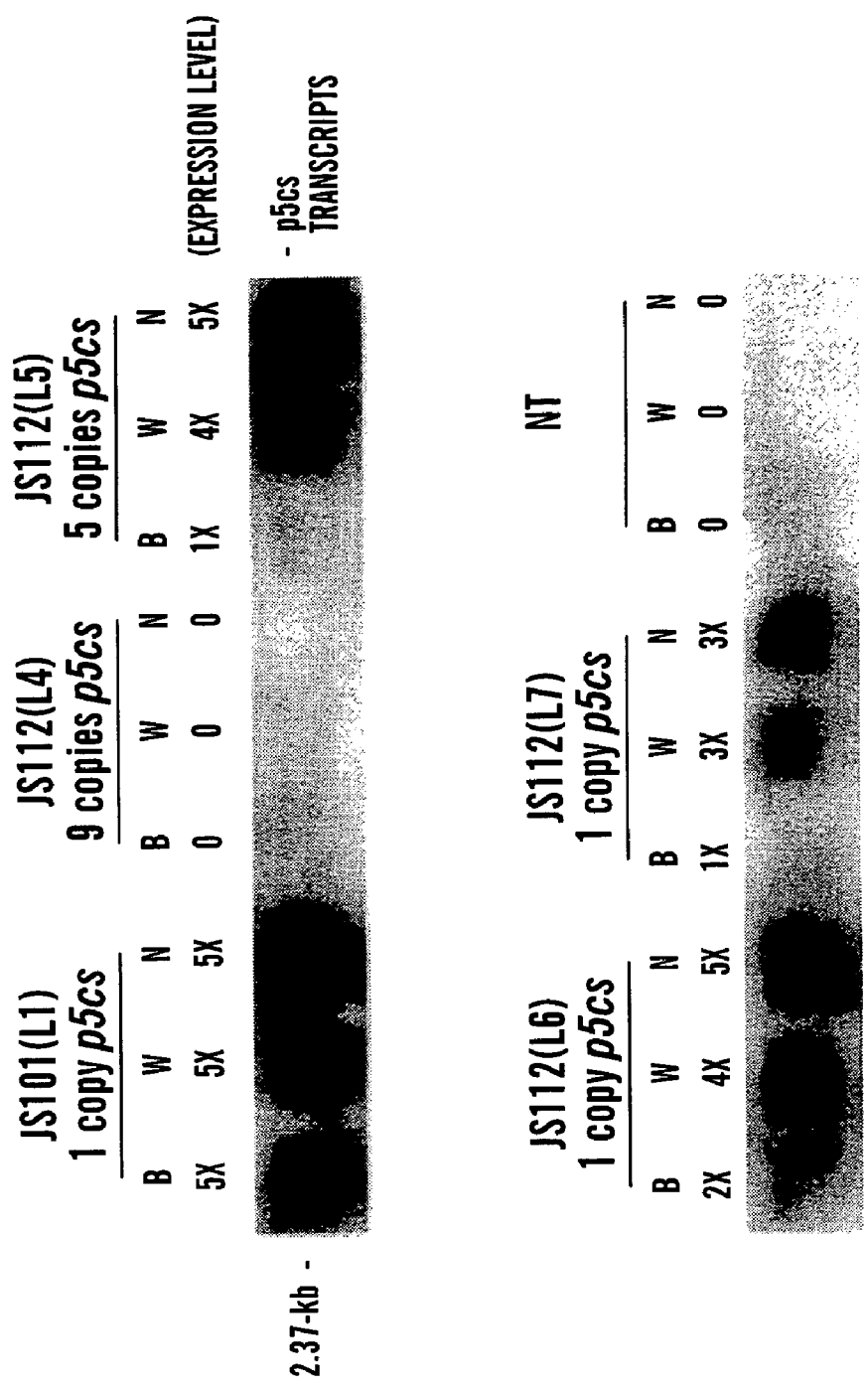
FIG. 3 shows constitutive or stress-inducible expression of p5cs transgene as determined by Northern blot hybridization analysis. The size (2.37 kb) of a p5cs RNA is indicated on the left-hand margin. B=basal level without stress; W=water stress; N=NaCl stress; NT=non-transgenic plants.

The p5cs expression was first analyzed at the mRNA level, and the results are shown in FIG. 3. Two-month-old $R_2$ plants were subjected to water-stress treatment by withholding water for 6 days (lane W), whereas non-stressed plants were supplied with water continuously and used for basal mRNA level (lane B) analysis. To detect the salt-stress-induced mRNA level (lane N), 200 mM NaCl solution was used to water p5cs-transgenic and uidA-transgenic plants (as control) for 48 hours. mRNA was only detectable in the p5cs-transgenic plants among tested lines. As can be seen in FIG. 3, the stress-induced expression level (lanes W or N) of the p5cs transgene reached a similar mRNA level (plants L5 & L6) as the constitutive expression in line L1. These data indicated that the p5cs mRNA production driven by SIPC was induced by water and salt stress, and the induction varies from 3- to 7-fold with different transgenic lines. L1 plants with constitutive p5cs expression (termed as Act1-p5cs plants in the following text) and L5 and L7 plants with stress-inducible p5cs expression (termed as SIPC-p5cs plants in the following text) were selected for further analysis.

Transgene expression is often correlated with the copy number and integration position of transgenes (position effect) in the genome (Meyer et al., "Homology Dependent Gene Silencing in Plants," *Annu. Rev. Plant Physiol. Plant Mol. Biol.*, 47:23–48 (1996), which is hereby incorporated by reference). As shown in FIG. 3, p5cs transcript was not detected in Line 4 (L4), which may be due to the transgene silencing resulting from high copy number (9 copies) of the p5cs transgene (Matzke et al., "How and Why do Plants Inactivate Homologous Transgenes?," *Plant Physiol.*, 107: 679–685 (1995), which is hereby incorporated by reference). On the other hand, L5 (5 copies) had a moderate level of p5cs transcript. In terms of position effect, the expression level of L7 (1 copy of transgene) was lower than that of L6 (also 1 copy of transgene). This suggests that an unfavorable position effect may be lowering the transgene expression in L7.

Example 9

Free Proline Level in Transgenic Rice Plants

One $R_2$ line of Act1-p5cs plants (L1) and two $R_2$ lines of SIPC-p5cs plants (L5 and L7) were used to determine the free proline content. The values listed in Table 1 include the proline level produced as a result of the expression of the transgene and the endogenous gene.

TABLE 1*

| Days of Water Stress | Water Content (%) in Soil | JS110 (L3) 7 copies uidA SIPC-uidA (control) | JS102 (L1) 1 copy p5cs Act1-P5CS | JS112 (L5) 5 copies p5cs SIPC-P5CS | JS112 (L7) 1 copy p5cs SIPC-P5CS |
|---|---|---|---|---|---|
| 0 | 35 | 4.2 ± 0.6 (100) | 13.4 ± 1.2 (319) | 5.8 ± 0.8 (138) | 5.1 ± 0.6 (121) |
| 5 | 21 | 8.8 ± 1.2 (100) | 28.6 ± 2.6 (325) | 16.4 ± 1.8 (186) | 12.8 ± 1.4 (145) |
| 8 | 10 | 31.5 ± 2.6 (100) | 72.4 ± 3.6 (210) | 63.3 ± 2.6 (182) | 58.3 ± 2.3 (169) |
| 8 d/0 d | | 7.5 | 5.4 | 10.9 | 11.4 |

| Days of NaCl Stress | | JS110 (L3) | JS102 (L1) | JS112 (L5) | JS112 (L7) |
|---|---|---|---|---|---|
| 0 | | 4.6 ± 0.8 (100) | 14.5 ± 1.4 (315) | 6.2 ± 1.0 (135) | 5.5 ± 1.1 (120) |
| 2 | | 24.6 ± 1.4 (100) | 52.6 ± 3.6 (214) | 42.5 ± 3.3 (173) | 33.5 ± 2.7 (136) |
| 3 | | 44.5 ± 3.4 (100) | 96.3 ± 4.7 (216) | 85.4 ± 4.2 (192) | 72.5 ± 3.6 (163) |

*For the top half of the table, three-month-old $R_2$ rice plants were grown in the greenhouse and subjected to water stress for 5 days or 8 days. For the bottom half of the table, three-month-old plants were watered with 200 mM NaCl solution for 2 or 3 days. Zero day represents the results of non-stressed plants. Proline content is shown as µmole/g fresh weight. Mean ± SE represents the average of 8 plants. Numbers inparentheses are the percentages of proline content in transgenic plants compared to control plants (L3), which have no p5cs transgene (represented by 100).

Before water-stress treatments (0 day), the proline level produced by the constitutive expression of the p5cs transgene (L1) reached 319%, the value of the L3 control plant. When a stress-inducible promoter (SIPC) was used, the proline level only reached 121% (L7) and 138% (L5) that of L3, respectively. However, as the stress proceeded, the proline level of lines L5 and L7 increased at a relatively higher rate and reached a final level approaching that of line L1 after 8 days of water stress.

For salt stress, the results shown in the bottom half of Table 1 were generally similar to those of water-stress treatment. In three different p5cs-transgenic lines, the proline content was 120% to 315% that of the control plant (L3) level before stress. After 3 days of NaCl stress, the proline content of the transgenic lines reached 163% to 216% that of the control plants. The proline assay also indicated that the endogenous proline production (in L3 plants) was induced by both water and salt stress. The increase of endogenous proline level induced by stress was most likely the result of both an increase in biosynthesis and a reduced loss due to oxidation. It has been indicated using metabolic labeling studies that most of the proline accumulated in plants in response to stress is the result of enhanced synthesis from glutamate (Kishor et al., "Overexpression of $\Delta^1$-pyrroline-5-carboxylate Synthetase Increases Proline Production and Confers Osmotolerance in Transgenic Plants," *Plant Physiol.,* 108:1387–1394 (1995), which is hereby incorporated by reference).

Example 10

Growth Performance of Seedlings Under Polyethylene Glycol (PEG)- or NaCl-Stress Conditions The above results demonstrated that the p5cs transgene was expressed as shown by increased mRNA level and increased proline accumulation. To address whether p5cs expression would have any beneficial effect on the growth performance of transgenic plants, a test for growth performance of $R_2$ seedlings under PEG- and water-stress conditions was carried out. Both non-transformed (NT) plants, which were regenerated following the same regeneration procedure, and the uidA transgenic plants as controls were chosen.

PEG is thought to create a water-stress condition (Corcuera et al., "Proline Metabolism in *Solanum tuberosum* Cell Suspension Cultures Under Water Stress," *J. Plant Physiol.,* 134:290–293 (1989), which is hereby incorporated by reference). 10% PEG8000 dissolved in half-strength (½) MS medium was used to germinate the rice seedlings. After 2 weeks of growth, all three lines of p5cs-transgenic seedlings (L1, L5, L7) showed increased tolerance to PEG stress (Table 2) and resulted in a larger increase in fresh shoot weight (50% to 95% higher than NT), and fresh root weight (29% to 62% higher than NT).

TABLE 2[†]

| Rice Line | Fresh Shoot Wt (mg/plant) | | Fresh Root Wt (mg/plant) | | Comparison | t Value* in NaCl-Stress Expt. | |
|---|---|---|---|---|---|---|---|
| | PEG | NaCl | PEG | NaCl | | Shoot Wt | Root Wt |
| NT | 20 ± 2 (100) | 30 ± 2 (100) | 21 ± 2 (100) | 38 ± 4 (100) | | | |
| JS110 (L3) | 21 ± 2 (105) | 32 ± 2 (107) | 22 ± 2 (105) | 41 ± 4 (108) | NT:L3 | 1.91 | 1.60 |
| JS102 (L1) | 33 ± 2 (165) | 42 ± 3 (140) | 29 ± 3 (138) | 57 ± 5 (150) | L1:L3 | 7.15 | 7.75 |
| JS112 (L5) | 39 ± 3 (195) | 58 ± 4 (193) | 34 ± 3 (162) | 66 ± 6 (174) | L5:L3 | 17.76 | 10.06 |

TABLE 2†-continued

| | Fresh Shoot Wt (mg/plant) | | Fresh Root Wt (mg/plant) | | | t Value* in NaCl-Stress Expt. | |
|---|---|---|---|---|---|---|---|
| Rice Line | PEG | NaCl | PEG | NaCl | Comparison | Shoot Wt | Root Wt |
| JS112 (L7) | 30 ± 3 (150) | 39 ± 3 (130) | 27 ± 2 (129) | 52 ± 5 (137) | L7:L3 | 5.20 | 5.13 |

*As compared to the t values of Student's distribution table, $t_{0.05(n\ =\ 10)} = 2.10$ and $t_{0.01(n=10)} = 2.88$. A statistical analysis (t-test) showed that there was no significant difference for comparing NT with L3 (NT:L3) because the value was lower than 2.10. All other comparisons showed significant differences because the values were higher than 2.88.
†Fresh shoot and root weights are in mg/plant. Means ± SE represents the average value of 10 plants. Numbers in parentheses are the percentages of transgenic plants as compared to control plants (NT), represented by 100. Although the $R_2$ plant population probably included segregated nontransgenic plants, they were all treated as transgenic plants in data collection and statistical analysis. NT, transformation procedure-derived non-transgenic plants. The spread of data within each set of 10 plants was rather small. For example, the actual values of the fresh shoot weight often JS110 (L3) plants in the NaCl-stress experiment were: 28, 29, 29, 31, 32, 33, 34, 34, 35 and 35.

For NaCl stress, the plantlets were first grown in ½ MS medium containing 200 mM NaCl for four weeks. After this period, the p5cs-transgenic seedlings showed significantly (P<0.01) higher tolerance to NaCl stress and resulted in an increase of 30% to 93% in fresh shoot weight and 37% to 74% in fresh root weight in three different p5cs-transgenic lines (Table 2). In conclusion, these assays demonstrated that the p5cs-transgene expression resulted in an increased tolerance to both PEG and NaCl stresses.

Example 11

Growth Performance of Transgenic Plants Under Water-Stress Condition

Next, growth performance of $R_2$ plants in soil was tested. Since there was no significant difference in growth performance between NT plants and uidA plants in seedlings tested (Table 2), the uidA plants (L3) were chosen as more suitable control plants for the following experiment, because they also contained bar and the same promoter cassette as the p5cs-transgenic plants.

Before initial water stress, all the 3-week-old plants including the L3 control plants, were tested for Basta resistance. Healthy, Basta-resistant plants with similar plant height were selected for analyzing growth performance. Under non-stress conditions in soil, no significant differences were observed between p5cs-containing transgenic plants and SIPC-uidA control plants in their growth performance during the entire period of the experiment. Upon withholding water from the trays, the absolute water content in the soil decreased from 35% to 12% after 7 days of water stress. Following 2 cycles of the water stress, the leaves of SIPC-uidA control plants started to turn yellow, and the Act1-p5cs plants showed low-growth rate, whereas the SIPC-p5cs plants with a stress-inducible promoter showed healthy growth. After 4 cycles of water stress, more severe symptoms, such as leaf chlorosis (in both control and Act1-p5cs plants) or death of leaf tips (in control plants only), were found. The SIPC-p5cs plants still showed a high rate of growth and less-severe leaf chlorosis. Data in Table 3 (top half) show the average fresh shoot weight and fresh root weight of the plants after 4 cycles of 7 days of water stress.

TABLE 3†

| Rice Line | Promoter | Fresh Shoot Wt (mg/plant) | Fresh Root Wt (mg/plant) | Comparison | t Value* in Water-Stress Expt. | |
|---|---|---|---|---|---|---|
| | | | | | Shoot Wt | Root Wt |
| JS110 (L3) | Inducible | 300 ± 20 (100) | 90 ± 20 (100) | L1:L3 | 9.54 | 3.21 |
| JS102 (L1) | Constitutive | 550 ± 60 (183) | 130 ± 20 (144) | L5:L3 | 14.22 | 8.05 |
| JS112 (L5) | Inducible | 940 ± 100 (310) | 220 ± 30 (224) | L7:L3 | 4.97 | 6.22 |
| JS112 (L7) | Inducible | 730 ± 60 (243) | 170 ± 20 (189) | L1:L5 | 7.64 | 5.88 |

| Transgenic Line | Promoter | Fresh Shoot Wt (mg/plant) | Fresh Root Wt (mg/plant) | Comparison | t Value* in NaCl-Stress Expt. | |
|---|---|---|---|---|---|---|
| | | | | | Shoot Wt | Root Wt |
| JS110 (L3) | Inducible | 320 ± 40 (100) | 70 ± 10 (100) | L1:L3 | 5.68 | 4.18 |
| JS102 (L1) | Constitutive | 580 ± 100 (181) | 110 ± 20 (157) | L1:L5 | 6.03 | 7.79 |
| JS112 (L5) | Inducible | 1030 ± 140 (322) | 240 ± 30 (343) | L5:L3 | 11.72 | 11.92 |
| JS112 (L7) | Inducible | 870 ± 150 (272) | 180 ± 30 (257) | L7:L3 | 7.83 | 7.67 |

*As compared to the t values of Student's distribution table, $t_{0.05\ (n-6)} = 2.23$ and $t_{0.01(n-6)} = 3.17$. All values higher than 3.17 are significant.
†Fresh shoot and root weights are in mg/plant. Means ± SE represents the averages of 6 plants (Wt). Values in parentheses are the percentages of p5cs-transgenic plants compared to control plants (L3), represented by 100. The spread of data within each set of 6 plants was rather small. For example, the actual values for the fresh shoot wt of six JS110 (L3) plants in the water-stress experiment (top half of table) were: 280, 282, 288, 315, 320 and 325; the actual values for the fresh shoot wt of six JS112 (L5) plants were: 840, 845, 860, 1025, 1045 and 1050.

The results indicated that under water stress, the SIPC-p5cs plants (L5 and L7), which contained a stress-inducible promoter to drive the p5cs expression, grew much faster as compared to Act1-p5cs plants (L1), which contained a constitutive promoter for driving the p5cs expression. The difference between using a stress-inducible promoter and a constitutive promoter was highly significant (P<0.01; t=5.88 to 7.64).

Example 12

Growth Performance of Transgenic Rice Plants Under Salt-Stress Condition

To create high soil salinity, 300 mM NaCl solution was added to the trays in which the pots were placed. At an early stage (10 days after the initial stress), the control plants (L3) started to wilt and the leaves began to turn yellow, whereas the p5cs transgenic plants still showed healthy growth. After 20 days of NaCl stress, the Act1-P5CS plants (L1) also started to wilt. Following 10 days of watering to allow recovery and an additional 10 days of 300 mM NaCl stress, more severe damage occurred in both control plants (L3) and Act1-p5cs plants. On the contrary, the leaves of SIPC-p5cs plants still remained green with a high rate of growth. The average fresh shoot weight and fresh root weight are shown in Table 3 (bottom half). These values indicated that SIPC-p5cs plants (L5 and L7) grew significantly larger (P<0.01; t=6.03 to 7.79) under salt-stress conditions than Act1-p5cs plants (L1) and control plants (L3), in spite of the finding that the proline level is lower in SIPC-p5cs plants. Of the two SIPC-p5cs lines, L5 was the better one. In conclusion, stress-inducible transgene expression in p5cs plants showed significant advantages over constitutive expression of the p5cs-transgene in growth of rice plants under salt- and water-stress conditions.

Example 13

Construction of Plasmids pJP21 and pJPM001

It has been reported that the DNA sequence from the nuclear matrix attachment region (MAR), when incorporated into the plasmid for transformation, can often reduce the copy number of the transgene as well as transformant-to-transformant variations in transgene expression (Spiker et al., "Nuclear Matrix Attachment Regions and Transgenic Expression in Plants," *Plant Physiol.,* 110:15–21 (1996); Mlynávová et al., "Approaching the Lower Limits of Transgenic Variability," *The Plant Cell,* 8:1589–1599 (1996), which are hereby incorporated by reference). Based on these reports, two plasmids were constructed, pJP21 and pJPM001, with and without a tobacco MAR sequence. The components of these two plasmids are as follows:

pJP21: ABRC1/Act-100P/H22I/Hva1/Pin2 3'//35S(P)/bar/ Nos 3' pJPM001: MAR//ABRC1/Act-100P/H22I/Hva1/Pin2 3'// 35S(P)/bar/Nos 3'//MAR where ABRC1 is the 49-bp ABA-responsive complex from the HVA22 promoter of barley; Act-100P is the minimal Act1 promoter (180 bp) from rice; H22I is the HVA22 intron from barley; HvaI is a barley cDNA that encodes a LEA3 protein; Pin2 3' is the 3' region of the potato protease inhibitor II gene; 35S (P) is the CaMV 35S promoter; and bar is the phosphinothricin acetyl transferase gene, which was used for selection. These plasmids were introduced into rice cells and the regenerated transgenic plants were analyzed. The results are shown in Table 4.

TABLE 4

Copy number of transgene in different primary transgenic lines ($R_0$) and the level of HVA1 protein.

| Plasmid Name | MAR Sequence | Number of Lines Analyzed | Single Copy | 2–3 Copies | >4 Copies | µg HVA1 per mg Soluble Leaf Protein* |
|---|---|---|---|---|---|---|
| pJP21 | − | 8 | 0 | 3 | 5 | 0 |
| pJPM001 | + | 16 | 4 | 4 | 8 | 2 to 3 |

*Basal level of HVA1 protein (without stress induction) was estimated by densitometric scanning of a Western blot. Based on the results to be shown in Table 5, the level of HVA1 protein was expected to be 3–8 times higher with the addition of ABA, or after drought or salt stress.

This preliminary result clearly showed that by including the MAR sequence in the plasmid (pJPM001) for transforming rice cells, the copy number of the transgene in transgenic rice plants is lower, and the level of HVA1 protein is higher, than those in plants transformed with a similar plasmid (pJP21) but without the MAR sequence. Thus, including the tobacco MAR sequence in the plasmid for transformation seemed to have a distinct advantage.

Example 14

Testing an ABA-Inducible Promoter in Driving Gus Expression in Transgenic Rice Plants The 49-bp ABA-response complex, ABRC1, from barley was used to construct plasmids whose expression in transgenic rice may be salt and drought inducible. Rice plants transformed with these plasmids may have advantages because a high level of transgene expression is induced only under salt- or drought-stress conditions so that expenditure of energy and building blocks for transgene expression under normal conditions can be avoided. Two different lengths of fragments from the 5' region of rice actin 1 gene (Act1), with or without Act1 intron, were tested for suitability as minimal promoters. Transient assays of promoter-Gus constructs in barley aleurone cells indicated that the shortest minimal promoter (Act1-100), joined to intron 1-exon 2-intron 2 of barley Hva22 (12), gave the highest level of ABA induction (the rice Act1 intron was not necessary for ABA induction). Thereafter, two types of expression plasmids were constructed containing Act1- 100 minimal promoter, intron 1-exon 2-intron 2 of Hva22, the gusA, with either one copy of ABRC1 or four tandem copies of ABRC1, and the bar genes as selection marker cassette. These two plasmids were used to transform rice cells by particle bombardment, and transgenic rice plants were regenerated. Three Southern hybridization-positive lines for each construct have been obtained. Quantitative assay of GUS activity of $R_1$ generation transgenic rice plants has been carried out before and after treatment of ABA, drought, and high concentrations of salt. The results are shown in Tables 5 and 6.

TABLE 5

ABA-induced GUS activity (4-MU, nmole/h/mg protein) in two-week-old $R_1$ seedlings of transgenic rice plants.

| ABA Treatment | GUS Activity* in Leaves or Roots of Plants | | | | | | | | | |
|---|---|---|---|---|---|---|---|---|---|---|
| | L2 | | L5 | | L7 | | L11 | | NT | |
| | leaves | roots | leaves | roots | leaves | roots | leaves | roots | Leaves | roots |
| None | 1 | 1 | 6 | 4 | 15 | 6 | 11 | 5 | <0.1 | <0.1 |
| +ABA | 1 | 1 | 22 | 26 | 73 | 48 | 41 | 33 | <0.1 | <0.1 |
| Fold Induction | 0 | 0 | 4 | 6 | 5 | 8 | 4 | 7 | 0 | 0 |

*GUS activity (mean of three independent experiments, and average of 3 plants per experiment) is expressed as nmol of 4-MU produced/h/mg protein. The standard error of the assay amounts to between 10–30% of the indicated values. 4-MU is 4-methylumbelliferone.

As can be seen from Table 5, the GUS activity in leaves of transgenic rice plants increased 4 to 5 fold by addition of ABA; GUS activity in roots increased 6 to 8 fold by addition of ABA.

Next, the transgenic plants and control plants were tested for response to salt stress. The plants in soil were watered with 150 mM NaCl solution for 2–4 days. The results in Table 6 show that the maximum GUS activity in leaves of transgenic plants increased 4-fold after salt stress, and the effect reached its peak after four days of NaCl treatment. The GUS activity in roots of transgenic plants increased 4-fold after salt stress, and the effect reached its peak after three days of NaCl treatment.

TABLE 6

NaCl-induced GUS activity in leaves and roots of $R_1$ transgenic rice plants[†].

| Days of NaCl Treatment | GUS Activity* in Leaves or Roots of Plants | | | | | | | | | |
|---|---|---|---|---|---|---|---|---|---|---|
| | L2 | | L5 | | L7 | | L11 | | NT | |
| | leaves | roots | leaves | roots | leaves | roots | leaves | roots | leaves | roots |
| 0 | 0.9 | 0.8 | 6 | 5 | 13 | 12 | 10 | 9 | <0.1 | <0.1 |
| 2 | 0.9 | 0.8 | 10 | 11 | 20 | 25 | 16 | 20 | <0.1 | <0.1 |
| 3 | 0.9 | 0.8 | 14 | 20 | 28 | 46 | 21 | 25 | <0.1 | <0.1 |
| 4 | 0.9 | 0.8 | 17 | 16 | 59 | 40 | 38 | 22 | <0.1 | <0.1 |
| Maximum Fold of Induction | 0 | 0 | 3 | 4 | 4 | 4 | 4 | 3 | 0 | 0 |

[†]Eight-week-old plants were grown in soil in the greenhouse. After withholding water for 1 day, the third leaf or 10% of the roots were collected for basal level of GUS activity (zero hour). The plants were then watered with 150 mM NaCl solution. At 2 days, 3 days, or 4 days, one leaf or 10% of roots were collected for assay of GUS activity.
*GUS activity (mean of three independent experiments, and average of 3 plants per experiment) is expressed as nmol of 4-MU produced/h/mg protein. The standard error of the assay amounts to between 10–30% of the indicated values.

Example 15

Figure 4:
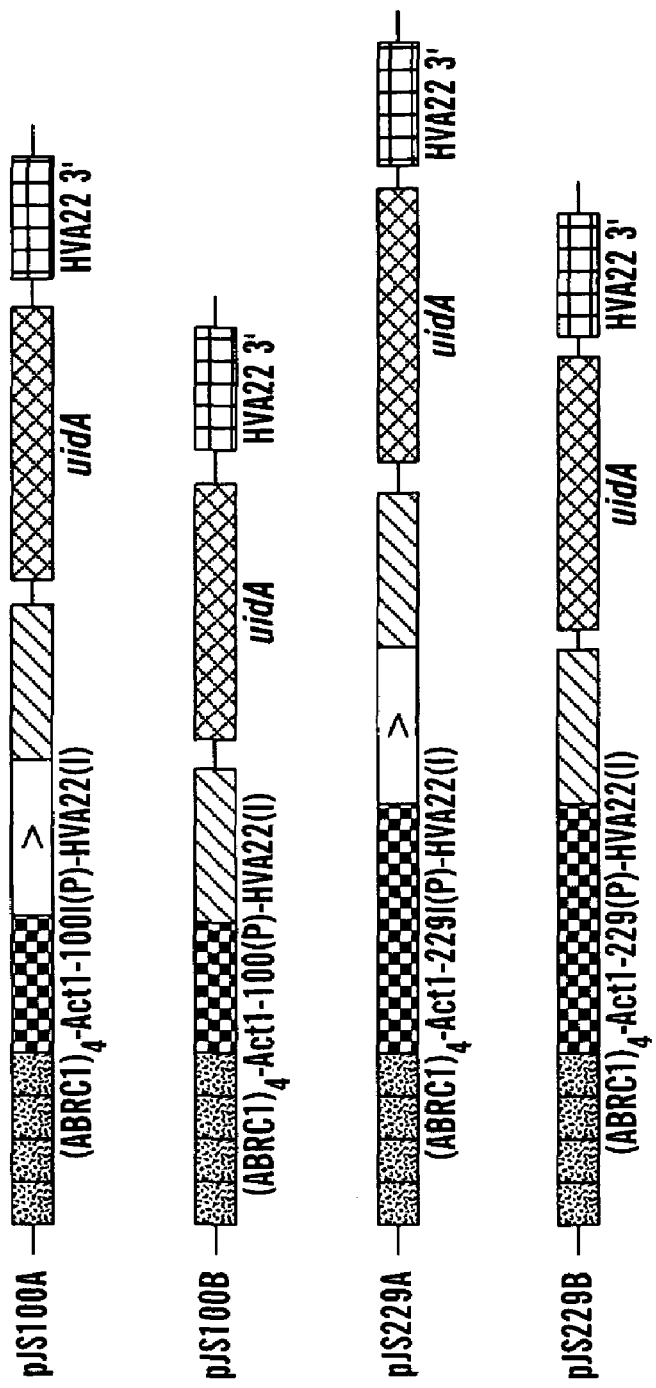
FIG. 4 shows a schematic diagram of the plasmids used for a transient assay of ABA-induced GUS activity in barley aleurone cells. For the construction of plasmid pJS100A, the Act1-100I(P) was inserted into pQS120 by replacing the Amy64 promoter. The Act1-100I(P) contains a truncated Act1 promoter (-100 to +560 including Act1 intron). Similarly, the construction of pJS100B started with Act1-100(P), which includes a truncated Act1 promoter (-100 to +80 without Act1 intron). The construction of pJS229A started with Act1-2291(P), which includes a truncated Act1 promoter (-229 to +560 including Act1 intron). The construction of pJS229B started with Act1-229(P), which includes a truncated Act1 promoter (-229 to +80 without Act1 intron).

Construction of Plasmids Containing (ABRC1)$_4$ Sequences, Different Lengths of Truncated Act1 Promoters, HVA22(I), and uidA, for Transient Assay of ABA-Induced GUS Activity in Barley Aleurone Cells For ABA-inducible uidA expression, a minimal promoter is required in addition to ABRC1, and HVA22(I) of the barley (*Hordeum vulgare* L.) HVA22 gene (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference). To elucidate the relationship between ABA-inducible uidA expression and different lengths of minimal promoters, four fragments of the rice Act1 promoter were isolated and tested as potential "minimal" promoters for transient assay of ABA-induced GUS activity in barley aleurone cells. A 789-bp Act1-2291 fragment with the Act1 intron, was isolated by HphI-EcoRI digestion from plasmid pBY505 (Wang et al., "A Vector for Inserting Foreign Genes and Selection of Transformed Rice Plants," *Rice Biotech. Quarterly*, 22:8 (1995), which is hereby incorporated by reference). The other three fragments (Act1-229, Act1-100I, and Act1-100) were isolated from the Act1-2291-derived intermediate plasmids by cutting the NruI and BstEII sites present in the Act1-2291 fragment (McElroy et al., "Isolation of an Efficient Actin Promoter for Use in Rice Transformation," *The Plant Cell*, 2:163–171 (1990), which is hereby incorporated by reference) in combination with other restriction sites located in the intermediate plasmids. These four fragments of truncated Act1 promoters were used to replace the Amy64 promoter in pQS120 plasmid (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference) which also contained four copies of ABRC1 elements, and one copy each of HVA22(I) of HVA 22, uidA, and HVA22 3' region, to create plasmids pJS229A, pJS229B, pJS 100A, and pJS100B (FIG. 4). The four truncated Act1 promoters and all the border regions between different functional elements were confirmed by sequence analysis. These four plasmids were used for transient assays of GUS activity in barley aleurone cells.

Example 16

Transient Assay of GUS Activity in Barley Aleurone Cells

Seeds of barley (*Hordeum vulgare* L.) cultivar Himalaya (1988 harvest; Department of Agronomy and Soils, Washington State University, Pullman, Wash.) were used. Preparations of embryoless half seeds and aleurone cells, particle bombardment, homogenization of the bombarded seed, GUS, and luciferase assays were conducted essentially as described previously (Lanahan et al., "A Gibberellin Response Complex in Cereal α-amylase Gene Promoters," *Plant Cell*, 4:203–211 (1992), which is hereby incorporated by reference).

Example 17

Test for Tissue Specificity and Histochemical Analysis

Leaves and roots from 10-day-old rice seedlings (*Oryza sativa* L. cv Kenfong) grown in solid MS (Murashige et al., "A Revised Medium for Rapid Growth and Bioassays With Tobacco Tissue Cultures," *Physiol. Plant*, 15:473–497 (1962), which is hereby incorporated by reference) medium were used as transformation materials and bombarded with tungsten particles coated with the pJS100B plasmid, essentially as described by Cao et al. "Regeneration of Herbicide Resistant Transgenic Rice Plants Following Microprojectile-Mediated Transformation of Suspension Culture Cells," *Plant Cell Reports*, 11:586–591 (1992), which is hereby incorporated by reference. The bombarded leaves and roots were transferred to fresh solid MS medium and cultured in a growth room (27° C. with photoperiod of 12 hours) for 2 days. Then, the transformed leaves and roots were induced in liquid MS medium in the presence of 20 μM ABA for 20 hours and subjected to histochemical staining with a solution containing 1 mM X-gluc and 50 mM sodium phosphate buffer (pH 7.0) as described by Jefferson et al., "GUS fusion: b-glucuronidase as a Sensitive and Versatile Gene Fusion Marker in Higher Plants," *EMBO J.*, 6:3901–3907 (1987), which is hereby incorporated by reference.

Example 18

Construction of Plasmids for Analyzing ABA- and/or Stress-Inducible uidA Expression in Transgenic Rice Plants A previous report (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference) indicated that four copies of ABRC1 confer ABA-responsive induction of uidA expression in barley aleurone cells four times higher than that with one copy. To compare the functional difference between one copy and four copies of ABRC1 in transgenic rice plants, two plasmids were constructed harboring either one copy or four copies of ABRC1. For construction of a plasmid containing one copy ABRC1, the ABRC1 fragment from plasmid pJS115 (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference) was isolated by EcoRI-XbaI digestion and subcloned into EcoRI-XbaI-digested pBluescript-KS(+/−). An Act1-100 promoter joined to the HVA22(I) (which is abbreviated as Act1-100P-HVA22(I)) was excised from pJS100B (see Table 7) by BamHI digestion and subcloned at the BamHI site downstream of ABRC 1 in pBluescript- KS(+/−) to produce the ABRC1-Act1-100P-HVA22(I) fragment.

TABLE 7

ABA-induced GUS activity in barley aleurone cells

| | Normalized relative GUS activity[a] (mean ± SE) | | |
|---|---|---|---|
| Constructs | ABA | + ABA | Fold induction |
| pJS100A | 3101 ± 452 | 14829 ± 3229 | 5 |
| pJS100B | 3677 ± 1012 | 77685 ± 3320 | 21 |
| pJS229A | 24571 ± 1963 | 45023 ± 4680 | 2 |
| pJS229B | 5627 ± 423 | 37454 ± 3465 | 7 |

[a]Normalized relative GUS activity was calculated based on luciferase activity (Lanahan et al., 1992); Each value ± SE (standard error) represents the average of 4 independent analyses. A maximum induction value is underlined.

Figure 5:
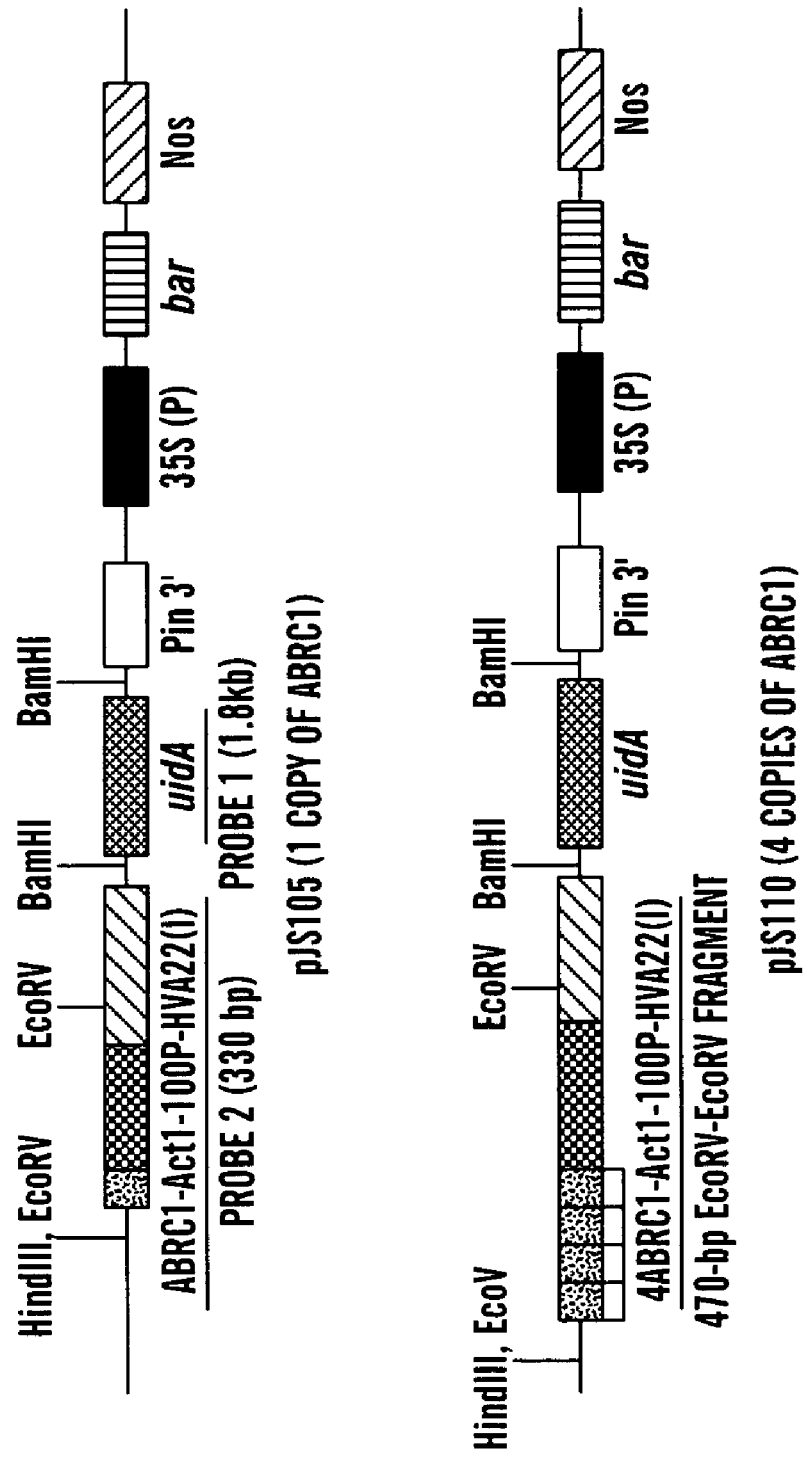
FIG. 5 shows a schematic diagram of plasmids pJS 105 and pJS110. Each plasmid consists of two gene expression cassettes: the uidA cassette, in which uidA expression is regulated by the ABRC1-Act1-100P-HVA22(I) promoter complex and the potato Pin 2 3' region, and the bar cassette, in which the bar gene is controlled by the CaMV 35S promoter and the nopaline synthetase gene (nos) 3' region, and serves as the selectable marker for transformation of rice. Only those restriction sites used for DNA digestion in DNA blot hybridization are indicated. HindIII is a unique site in these two plasmids.

Act1-100 was chosen as the minimal promoter (named as Act1-100P) because it was the best among the four fragments listed in FIG. 4, as determined by transient assay of GUS activity in barley aleurone cells. The fragment ABRC1-Act1-100P-HVA22(I) was further cloned into the Act1 5' region-deleted pBY505 to create pJS104 plasmid which contains ABRC1-Act1-100P-HVA22(I)/polylinker/Pin2 3'//CaMV 35S (P)/bar/Nos. The bar cassette, 35S (P)/bar/Nos, was used for selection of rice transformants. By using the same procedure (except that four tandem copies of ABRC1 were isolated from pQS120 (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference)) pJS 109, which contained 4ABRC 1-Act 1-100P-HVA22(I)/polylinker/Pin2 3'//35S (P)/bar/Nos, was also constructed. Both plasmids pJS104 and pJS109 may serve as expression vectors for construction of plasmids containing stress-tolerant genes. The GUS coding sequence (uidA) was cloned into the SmaI site of pJS104 and pJS109 to create pJS105 and pJS110, respectively (the components of the latter two plasmids are shown in FIG. 5). The plasmids pJS105 and pJS110 were used for transformation of rice and for testing ABA and/or stress-inducible uidA expression in the transgenic rice plants.

Example 19

Production of Transgenic Rice Plants

Calli were induced in LS medium (Linsmaier et al., "Organic Growth Factor Requirements of Tobacco Tissue Cultures," *Physiol. Plant*, 18:100–127 (1965), which is hereby incorporated by reference) from mature rice embryos (*Oryza sativa* L. cv Kenfong). Suspension cultures were initiated from embryogenic calli in liquid AA medium (Cao et al., "Assessment of Rice Genetic Transformation Techniques," In *Rice Biotechnology*, Toenniessen et al., eds, C.A.B. International, Oxon, UK, 175–198 (1991), which is hereby incorporated by reference). Fine suspension cells (subcultured for three days prior to bombardment) were bombarded with tungsten particles coated with either the pJS105 or the pJS110 plasmid, according to the procedure described by Cao et al. (Cao et al., "Regeneration of Herbicide Resistant Transgenic Rice Plants Following Microprojectile-Mediated Transformation of Suspension Culture Cells," *Plant Cell Reports*, 11:586–591 (1992), which is hereby incorporated by reference). Resistant calli were selected in KPR medium (Zhang et al., "Efficient Regeneration of Transgenic Plants from Rice Protoplasts and Correctly Regulated Expression of the Foreign Gene in the Plants," *Theor. Appl. Genet.*, 76:835–840 (1988), which is hereby incorporated by reference) supplemented with 8 mg L$^{-1}$ Bialaphos as selective agent, for six weeks (subcultured every two weeks). The resistant calli were transferred to MS regeneration medium containing 3 mg L$^{-1}$ Bialaphos to regenerate into plants. Regenerated plants were transplanted into sterilized soil and grown in the greenhouse (32° C. day/22° C. night with supplemental photoperiod of 10 hours).

The presence of the transgenes in regenerated rice plants was first indicated by the herbicide resistance of the plants. To test herbicide resistance, leaves on 3-month-old transgenic rice plants were painted on both sides with 0.25% (V/V) of the herbicide Basta (containing 162 g L$^{-1}$ glufosinate ammonium; Hoechst-Roussel Agri-Vet Co., Somerville, N.J.) and 0.05% (V/V) Tween-20. One week later, the resistant or sensitive phenotypes were scored.

Example 20

DNA Blot Hybridization Analysis of Transgenic Rice Plants

Genomic DNA from transgenic rice plants was prepared as described by Zhao et al., "Genome-Specific Repetitive Sequences in the Genus *Oryza*," *Theor. Appl. Genet.*, 78:201–209 (1989), which is hereby incorporated by reference. Eight μg of genomic DNA were digested with restriction enzymes, electrophoresed through 0.8% (for uidA probe) and 1.2% (for probe 2 shown in FIG. 5) agarose gels, and transferred to nylon membranes (NYTRAN, Schleicher & Schuell, Inc. Keene, N.H.). Probe preparation and hybridization were performed by following the manufacturer's instruction of non-radioactive DIG-labeling and detection kit (Boehringer Mannheim, Indianapolis, Ind.).

Example 21

RNA Blot Hybridization Analysis of Transgenic Rice Plants

Total RNA from leaves of $R_1$ transgenic rice plants was isolated as described by Hihara et al., "Isolation and Characterization of Two cDNA Clones for mRNA that are Abundantly Expressed in Immature Anthers of Rice (*Oryza sativa* L.)," *Plant Mol. Biol.*, 30:1181–1193 (1996), which is hereby incorporated by reference). Five μg of total RNA from the transgenic rice were subjected to electrophoresis in a 1.0% formaldehyde agarose gel. After electrophoresis, RNA was transferred to a nylon membrane (Boehringer Mannheim, Indianapolis, Ind.). The 1.8-kb GUS coding region was used as a probe and labeled with [α-$^{32}$P]dCTP using a random primers DNA labeling kit (GIBCO BRL, Rockville, Md.). Gel preparation, hybridization, and washing were carried out as described by Sambrook et al., *Molecular Cloning: A Laboratory Manual*, 2$^{nd}$ Ed., Cold Spring Harbor Laboratory Press, Cold Spring Harbor, N.Y. (1989), which is hereby incorporated by reference.

Example 22

ABA, Water Deficit, and NaCl Treatments of Transgenic Rices

For ABA treatment, seedlings of $R_1$ plants were used. Rice embryos of $R_1$ mature seeds both from transgenic and nontransgenic plants were germinated in solid half-strength MS and cultured in a growth room for five weeks for RNA blot hybridization or two weeks for assaying ABA-induced GUS activity. Then, the 5-week-old or 2-week-old $R_1$ plants were transferred to liquid half-strength MS medium containing 50 μM ABA for 20 hours in the growth room. For stress treatments (water deficit and NaCl), $R_1$ plants grown in soil were used. $R_1$ seeds were first germinated in half-strength MS medium for seven days, and were then transplanted into soil in pots (8×8 inches) with holes in the bottom. The pots were kept in flat-bottomed trays containing water. The seedlings were grown for an additional seven weeks before they were exposed to stress conditions. To induce water deficit, water was withheld from the trays for up to eight days. The absolute water content of the soil during the stress period and before treatment were determined. Non-stressed plants were supplied with water continuously from the trays. For NaCl treatment, water containing 150 mM NaCl solution was used to water 8-week-old plants including non-transgenic plants. Leaves and roots were collected from the same plant after different periods of stress treatments and used for assaying stress-induced GUS activity.

Example 23

Quantitative Assay of GUS Activity in Transgenic Rice Plants

To detect the GUS activity in $R_0$ plants before treatment and in $R_1$ transgenic rice plants after treatment with ABA, water deficit, and NaCl, a quantitative assay of GUS activity was carried out as described by Jefferson et al., "GUS Fusion: β-as a Sensitive and Versatile Gene Fusion Marker in Higher Plants," *EMBO J.*, 6:3901–3907 (1987), which is hereby incorporated by reference. Different leaves (adjacent) or roots from the same $R_1$ plant of each line were collected before treatment or at the different stages of treatments: 20 hours for ABA treatment, four, six, and eight days for water stress, and 48, 72, and 96 hours for NaCl treatment. Control experiments in parallel to ABA and NaCl treatments in the absence of ABA or NaCl were also performed to test possible injury effect on GUS activity. Collected leaves or roots were frozen immediately in liquid nitrogen and homogenized in extraction buffer (50 mM phosphate buffer, pH 7.0, 10 mM EDTA, 0.1% Triton X-100, 0.1% Sarkosyl, 10 mM β-mercaptoethanol and 25 μg ml$^{-1}$ PMSF). After centrifugation (12,000 rpm for 15 minutes, 4° C.), the crude extract, containing 20 μg of protein from leaves or roots, was directly used for spectrofluorometric assay. Protein concentration of the crude extract was determined by the dye-binding method of Bradford, "A Rapid and Sensitive Method for Quantitation of Microgram Quantities of Protein Utilizing the Principle of Protein-Dye Binding," *Anal. Biochem.*, 72:248–254 (1976), which is hereby incorporated by reference, with a protein assay reagent (Bio-Rad, Hercules, Calif.).

Example 24

The Shortest Truncated Act1 Promoter (Act1-100P) Confers the Highest ABA Induction in Barley Aleurone Cells In order to get ABA- and stress-inducible gene expression in transgenic rice plants, a truncated promoter (termed as "minimal promoter") is required, in addition to ABRC1 and HVA22(I) of HVA 22 gene. Before stable transformation of rice, transient expression assay of ABA-induced GUS activity was first performed in barley aleurone cells by using four different lengths of truncated Act1 promoters as the "minimal" promoters. The results (Table 7) indicated that the plasmid with the shortest promoter (Act1-100P) shows not only the highest induction (21-fold), but also the highest GUS activity after exogenous ABA application. The Act1 intron is not necessary for ABA-inducible uidA expression. In fact it inhibits uidA expression when the HVA22 intron is also present in the plasmid (see Table 7).

Tissue specificity of uidA expression driven by the ABA-responsive promoter complex [4ABRC1-Act1-100P-HVA22(I)] was also tested. After histochemical analysis following ABA induction, blue spots were observed in the detached leaves and roots bombarded with plasmid pJS100B. This result indicated a lack of tissue specificity for ABA-inducible uidA expression driven by the ABA-responsive promoter complex. According to the results mentioned above, Act1-100P was used as a minimal promoter for plasmid constructs suitable for stable transformation of rice plants.

Example 25

Figure 6:
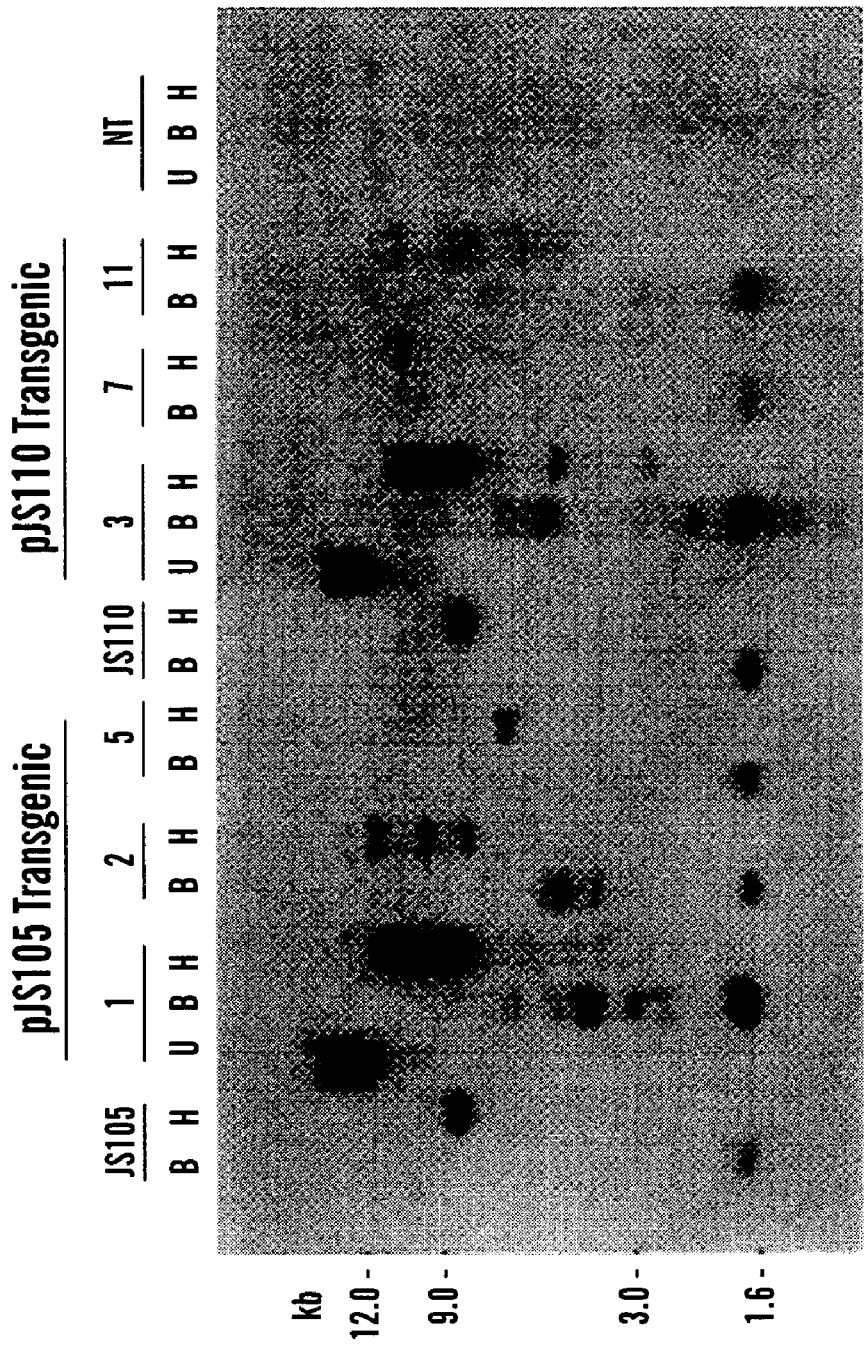
FIG. 6 shows the Southern Hybridization Analysis of gusA-transgenic rice plants. Eight µg of rice genomic DNA were digested by BamHI (two sites in the plasmids) or HindIII (a unique site in the plasmids) and separated in a 0.8% agarose gel. A DIG-labeled, 1.8-kb GUS coding region (probe 1, see FIG. 5) was used as the probe. Molecular sizes (kb) of 1 kb DNA ladder (GIBCO BRL, Life Technology, Inc., Rockville, Md.) are indicated on the left side. B=BamHI; H=HindIII; U=undigested; NT=DNA from non-transgenic plants.

Production of Transgenic Rice Plants and Southern Blot Hybridization Analyses Two plasmids, pJS105 (containing one copy of ABRC1) and pJS10 (containing four copies of ABRC1), were constructed for expression of uidA in transgenic rice plants. The structures of these two plasmids are shown in FIG. 5. After particle bombardment of suspension cells by using the two plasmids, eight Basta-resistant and Southern blot-positive lines were regenerated, of which six (three lines for each plasmid) showed the correct hybridization pattern. The other two lines had rearranged bands, so they were not further studied. The six desired transgenic lines were all fertile and their $R_1$ generation were used for further analyses. The results of Southern blot hybridization with the 1.8-kb uidA coding region as the probe (probe 1, FIG. 5) are shown in FIG. 6. Both rice genomic DNA and plasmid DNA were digested by BamHI or HindIII. BamHI digestion released a 1.8-kb hybridizing band corresponding to the size of uidA. HindIII is a unique site in the plasmids pJS105 and pJS110. Thus, each hybridization band created by HindIII digestion represents one copy of transgene uidA, except in cases when HindIII fragments cannot be resolved. Each line has its own specific hybridization pattern except the expected 1.8-kb band, indicating that these six transgenic lines were derived from independent transformation events.

Figure 7:
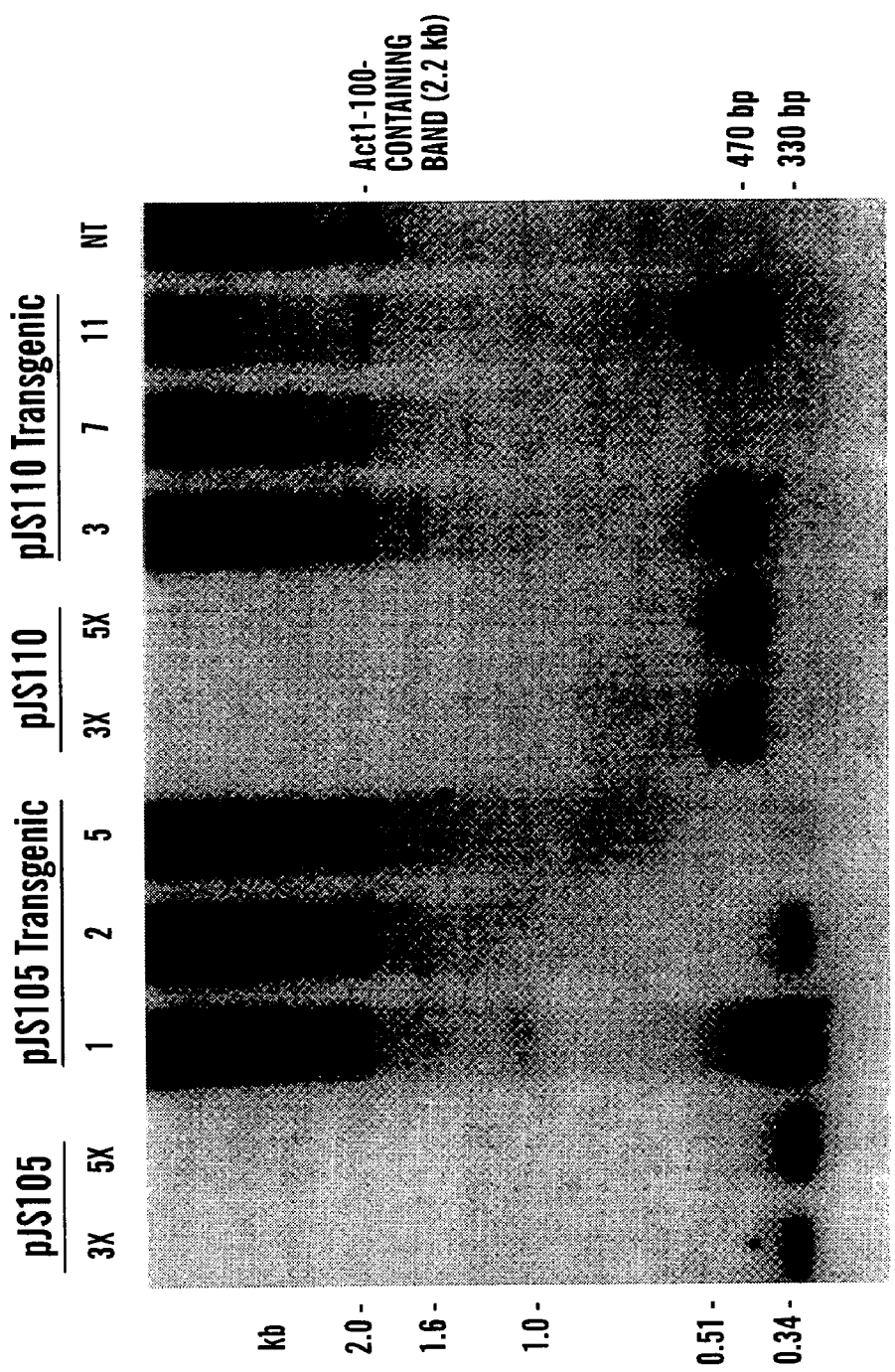
FIG. 7 shows the Southern Hybridization Analysis of gusA-transgenic rice plants. Eight µg of genomic DNA were digested by EcoRV (see EcoRV sites in FIG. 5) and the digested DNA was separated in a 1.2% agarose gel. A DIG-labeled, 330-bp of probe 2 (indicated in FIG. 5) was used as the probe. Molecular sizes of 1 kb DNA ladder are indicated on the left side. 3x and 5x plasmid DNA represent 3 and 5 genome equivalents of DNA relative to 8 µg of rice genomic DNA, respectively.

To verify that one copy of ABRC1 and four copies of ABRC1 were also integrated into the genome of transgenic rice plants, another Southern blot hybridization was conducted by using the 330-bp probe 2 (See FIG. 5). The results (FIG. 7) indicated that transgenic lines 1, 2, and 5 contain one copy of ABRC1 corresponding to the size (330-bp) of the expected band of pJS105, whereas lines 3, 7, and 11 contain four copies of ABRC1 corresponding to the size (470-bp) of the expected band of pJS110. This result also showed that the one copy of ABRC1 or four copies of ABRC1, fused to the Act1-100P with the HVA22(I), were integrated into the rice genome. The copy number of the transgenes was estimated both by HindIII digestion, which has only one restriction site in the plasmids (FIG. 6), and by using the Act1-100P-containing band as internal standard. Previous work (McElroy et al., "Isolation of an Efficient Actin Promoter for Use in Rice Transformation," *The Plant Cell*, 2:163–171 (1990), which is hereby incorporated by reference) indicated the presence of only one copy of Act1 gene in the rice genome. Since there is also one copy of the Act1-100P in plasmids pJS105 and pJS110, the ratio of the intensity of hybridization bands (the 330-bp band for pJS105 transgenic lines, and 470-bp band for pJS110 transgenic lines) to the band (2.2-kb) corresponding to that of non-transgenic plants (NT) should give the copy number of the transgene in a given transgenic plant (Table 8).

TABLE 8

Approximate copy number of transgenes in pJS105- and pJS110-transgenic lines

|  | pJS105 Transgenic | | | pJS110 Transgenic | | |
|---|---|---|---|---|---|---|
| Lines | 1 | 2 | 5 | 3 | 7 | 11 |
| Transgene Copy No. | 9 | 3 | 1 | 7 | 1 | 5 |

Example 26

GUS Activity in $R_0$ Transgenic Rice Plants

Figure 8:
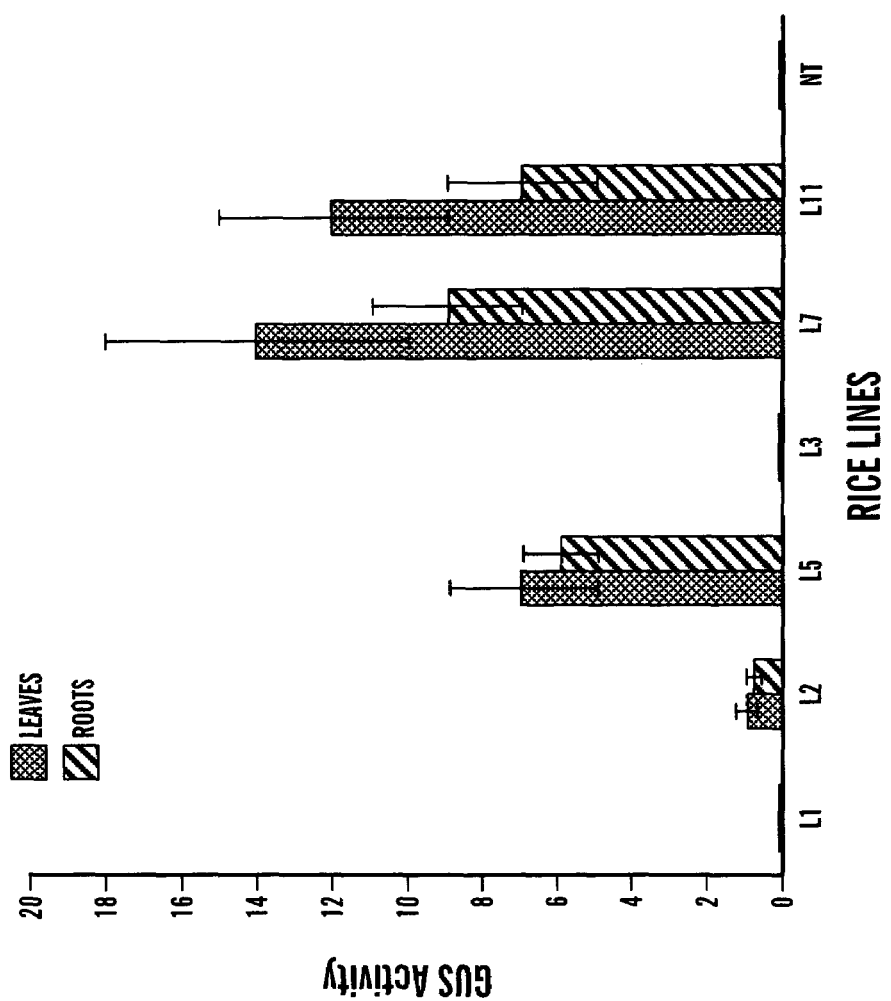
FIG. 8 shows GUS activity in the $R_0$ transgenic plants without any treatment. L1, L2, and L5 represent pJS105-transgenic line 1, 2, 5; and L3, L7, and L11 represent pJS 110-transgenic line 3, 7,11, respectively. Mean±SE values of GUS activity (4-MU nmol h$^{-1}$ mg proteins$^-$) are.

The promoter complex in plasmids pJS105 and pJS110 is composed of ABRC1, Act1-100P minimal promoter, and HVA22(I), in which Act1-100P promoter plays an important role in conferring basal level of uidA expression. Before starting to test for ABA- and stress-induced GUS activity, the basal level of GUS activity in 4-month-old $R_0$ transgenic plants was first examined. The results are shown in FIG. 8. Of the six transgenic lines, three lines (L5, L7, L11) showed high levels of GUS activity, and L2 showed low activity (<1 nmol h-1 mg protein-1). No GUS activity was detected in either leaves or roots of L1 and L3. Lines L2 and L5 (pJS105 transformants) and lines L7 and L1 (pJS110 transformants) were used for assaying ABA- and stress-inducible uidA expression.

Example 27

ABA-, Water Deficit-, and NaCl-Induced uidA mRNA Level in Transgenic Rice Plants In order to test the ABA- or stress-inducible uidA expression, the transcript level of uidA transgene in $R_1$ leaves, before or after water deficit treatment for six days in the greenhouse, was first examined. Three transgenic lines (L5, L7, L11) were found to express uidA. L5 from pJS105 construct and L7 from pJS110 construct were selected for further treatments and analyses. ABA and NaCl were also found to induce uidA expression (FIG. 9). By densitometry tracing, the induction level varies from 6- to 8-fold. No uidA transcripts were detected in $R_1$ leaf RNA from the other two Southern blot-positive lines (L1 and L3) or from nontransgenic plants even after water deficit treatment.

Example 28

ABA-Induced GUS Activity in Transgenic Rice Plants

A previous report (Shen et al., "Functional Dissection of an Abscisic Acid (ABA)-Inducible Gene Reveals Two Independent ABA-Responsive Complexes Each Containing a G-Box and Novel cis-Acting Element," *The Plant Cell*, 7:295–307 (1995), which is hereby incorporated by reference) indicated that ABRC1 confers a high degree of ABA induction for gene expression by a transient assay in barley aleurone cells. To examine the ABA-induction level of uidA expression conferred by the ABA-responsive promoter complex, ABRC1-Act1-100P-HVA22(I), in transgenic rice leaves and roots, a quantitative assay of GUS activity before and after ABA treatment of 2-week-old seedlings was carried out. At the 2-week stage, most $R_1$ seedlings had two normal-sized leaves. Of 10 plants tested, eight showed GUS activity and ABA inducibility. A lower leaf of an $R_1$ seedling was cut off and used for GUS activity assay before applying exogenous ABA. An upper leaf of the same seedling was collected for assaying ABA-inducible uidA expression after supplying 50 μM ABA for 20 hours. The results of this analysis are given in FIG. 10. It was shown that the absolute level of GUS activity in pJS110-transformed plants is higher than that of pJS105-transformed plants both before and after ABA induction. A control experiment using upper leaves of L7 (with the highest GUS activity) after collection of the lower leaf was carried out in the absence of ABA and no increase of GUS activity was found. Thus, removing leaf tissues from plants did not show any adverse effect on GUS activity.

Example 29

Water Deficit-Induced GUS Activity in Transgenic Rice Plants

As mentioned previously, ABA mediates gene expression involved in plant physiological responses to stress such as drought and salinity. The ABA-induced uidA expression disclosed above provided encouragement to explore the water deficit-induced GUS activity in the transgenic rice. Before water deficit treatment, the third leaf from bottom and about one-tenth the amount of roots of 8-week-old $R_1$ plants with four to five leaves were collected and frozen in liquid nitrogen, and used for assaying the basal level of GUS activity. These plants were subjected to water deficit treatment for 4, 6, and 8 days. The other three leaves from the same plant used for assaying basal level were collected at 4, 6, and 8 days, respectively, after the treatment and used for testing the induced activity. At the same time, one-tenth the amount of roots was also collected at each time point following the leaf collection. Three plants for each line were used for each experiment to calculate the degree of induction of uidA expression by water deficit treatment. The results from three independent experiments are listed in Table 9.

TABLE 9

Water deficit-induced GUS activity in $R_1$ leaves and roots of transgenic rice plants

| | $H_2O$ | GUS activity (4-MU nmol $h^{-1}$ mg protein$^{-1}$, Mean ± SE) | | | | | | | | |
|---|---|---|---|---|---|---|---|---|---|---|
| | content | pJS105 Transgenic | | | | pJS110 Transgenic | | | | |
| Days of | of soil | L2 | | L5 | | L7 | | L11 | | NT |
| treatment | (%) | leaves | roots | leaves | roots | leaves | roots | leaves | roots | leaves | roots |
| 0 | 37 | 1 ± 0.2 | 0.9 ± 0.2 | 7 ± 3 | 6 ± 2 | 14 ± 4 | 13 ± 3 | 10 ± 3 | 7 ± 2 | 0.02 ± 0.01 | 0.01 ± 0.01 |
| 4 | 24 | 1 ± 0.2 | 0.9 ± 0.2 | 10 ± 3 | 11 ± 3 | 18 ± 4 | 28 ± 3 | 14 ± 4 | 16 ± 3 | 0.02 ± 0.01 | 0.01 ± 0.01 |
| 6 | 14 | 1 ± 0.2 | 0.9 ± 0.2 | 18 ± 4 | <u>34 ± 5</u> | 35 ± 6 | <u>88 ± 6</u> | 27 ± 6 | <u>41 ± 5</u> | 0.02 ± 0.01 | 0.01 ± 0.01 |
| 8 | 9 | 1 ± 0.2 | 0.9 ± 0.2 | <u>40 ± 6</u> | 31 ± 5 | <u>81 ± 7</u> | 80 ± 6 | <u>47 ± 7</u> | 38 ± 5 | 0.02 ± 0.01 | 0.01 ± 0.01 |
| 8 d/0 d | | 1 | | 6 | | 6 | | 5 | | 1 | |
| 6 d/0 d | | | 1 | | 6 | | 7 | | 6 | | 1 |

Mean ± SE values of the GUS activity were calculated from the results of three independent experiments and three plants used for each experiment. $R_1$ plants were grown in a greenhouse and treated without water for four, six and eight days.
0 day represents the basal level before water deficit treatment.
8 d/0 d indicates the induction fold of GUS activity in rice leaves by withholding water for eight days, and 6 d/0 d indicates the induction fold in rice roots by withholding water for six days.
NT = nontransgenic.
Maximum induction values are underlined.

After 4 days of treatment, GUS activity in rice leaves increased only slightly. With an increase of treatment days, GUS activity increased rapidly and reached a peak at 8 days, resulting in 5- to 6-fold induction. Beyond 8 days, the treated leaves started to wilt. In rice roots, the GUS activity reached a peak after six days. A longer treatment (e.g., eight days) gave a slightly reduced level of uidA expression in the roots of transgenic rice by withholding water.

Example 30

NaCl-Induced GUS Activity in Transgenic Rice Plants

To test the extent of induction of uidA expression by salt treatment, 150 mM NaCl solution was used to create salinity stress condition. Water was withheld for 24 hours from eight-week-old plants with four to five leaves grown in the greenhouse, and then 150 mM NaCl solution was added to the plant-containing pots and the tray. The NaCl solution was changed every 24 hours. Samples were collected in the same way as in the water deficit treatment except that the third leaf of each plant used for assaying the basal level of GUS activity was collected after 24 hours of withholding water (named 0 h treatment by NaCl). Table 10 indicates the results of this analysis in the leaves and roots of transgenic rice.

TABLE 10

NaCl-induced GUS activity in $R_1$ leaves and roots of transgenic rice plants

GUS activity (4-MU nmol $h^{-1}$ mg protein$^{-1}$)

| | pJS105 Transgenic | | | | pJS110 Transgenic | | | | | |
|---|---|---|---|---|---|---|---|---|---|---|
| Hours of NaCl | L2 | | L5 | | L7 | | L11 | | NT | |
| treatment | leaves | roots | leaves | roots | leaves | roots | leaves | roots | leaves | roots |
| 0 | 0.9 ± 0.2 | 0.8 ± 0.2 | 6 ± 2 | 5 ± 1 | 13 ± 3 | 12 ± 2 | 10 ± 2 | 9 ± 2 | 0.02 ± 0.01 | 0.01 ± 0.01 |
| 48 | 0.9 ± 0.2 | 0.8 ± 0.2 | 10 ± 3 | 11 ± 3 | 20 ± 4 | 25 ± 4 | 16 ± 4 | 20 ± 4 | 0.02 ± 0.01 | 0.01 ± 0.01 |
| 72 | 0.9 ± 0.2 | 0.8 ± 0.2 | 14 ± 3 | <u>20 ± 5</u> | 28 ± 6 | <u>46 ± 6</u> | 21 ± 4 | <u>25 ± 5</u> | 0.02 ± 0.01 | 0.01 ± 0.01 |
| 96 | 0.9 ± 0.2 | 0.8 ± 0.2 | <u>17 ± 4</u> | 16 ± 3 | <u>59 ± 7</u> | 40 ± 4 | <u>28 ± 5</u> | 22 ± 3 | 0.02 ± 0.01 | 0.01 ± 0.01 |
| 96 h/0 h | 1 | | 3 | | 4 | | 3 | | 1 | |
| 72 h/0 h | | 1 | | 4 | | 4 | | 3 | | 1 |

Mean ± SE values of NaCl-induced GUS activity were calculated from the results of three independent experiments and three plants used for each experiment. 8-week-old $R_1$ plants were grown in the greenhouse. After withholding water for 24 hours, the third leaf or one-tenth the amount of roots were collected and used for a basal level test of GUS activity (0 h). Then, the plants were supplied with 150 mM NaCl solution. At 48 hours, 72 hours, and 96 hours, the other three leaves or one-tenth the amount of roots were collected respectively, and used for assaying NaCl-induced GUS activity.
Maximum induction values are underlined.

As compared to the results of ABA and water deficit treatments, the GUS activity and induction level were both lower. Similar to the water deficit treatment, the NaCl-induced GUS activity in the roots of transgenic rice plants reached its peak at 72 hours of treatment. A longer treatment (such as 96 hours) showed a slightly reduced level of uidA expression. A control experiment using leaves collected at 48 hours, 72 hours, and 96 hours after cutting the first leaf was also performed in the absence of NaCl and no increase of GUS activity was observed. Thus, removing leaf tissues from plants did not show any adverse effect on GUS activity.

In conclusion, ABA, water deficit, and 150 mM NaCl induced uidA expression both at the RNA and protein level (GUS activity), conferred by the ABA-induced promoter in transgenic rice plants. Transgenic rice plants harboring the plasmid with four copies of ABRC1 exhibited 50% to 200% higher GUS activity than those with one copy of ABRC1 among the tested transgenic rice lines. The Act1-100P minimal promoter coupled with ABRC1 and HVA22(I) of barley HVA22 gene conferred ABA- and stress-inducible uidA expression in transgenic rice. These results suggest that the expression vectors pJS104 (containing one copy of ABRC1) and pJS109 (four copies of ABRC1) can be used for other plasmid constructions to produce stress-induced osmotolerant transgenic rice plants.

Example 31

Water Stress or Salt Stress Transgenic Rice Plants

Different stress treatments and exogenous ABA application caused different extents of induction of uidA expression both in transgenic rice leaves and roots. In these Examples, water deficit treatment caused the highest induction of GUS activity about 5- to 6-fold in rice leaves, followed by ABA application with a 4- to 5-fold increase, and NaCl treatment with 3- to 4-fold increase of GUS activity. In roots, ABA treatment resulted in the highest induction of GUS activity with a 7- to 8-fold increase, followed by water deficit treatment with a 6- to 7-fold induction, and NaCl treatment with a 3- to 4-fold increase.

Strong and constitutive promoters are beneficial for high-level expression of selectable marker genes which is necessary for efficient selection and generation of transgenic plants. However, constitutively active promoters are not always desirable for plant genetic engineering because constitutive over-expression of a transgene may compete for energy and building blocks for synthesis of proteins, RNA, etc., which are also required for plant growth under normal conditions. Either one copy of ABRC1 or four tandem copies of ABRC1 coupled with Act1-100P and HVA22(I) of HVA22 gene confer ABA- and stress-induced uidA expression in transgenic rice.

Transgene expression in transgenic plants is often correlated with copy number (Hobbs et al., "Transgene Copy Number Can Be Positively or Negatively Associated With Transgene Expression," Plant Mol. Biol., 21:17–26 (1993); Matzke et al., "Homology-dependent Gene Silencing in Transgenic Plants; Epistatic Silencing Loci Contain Multiple Copies of Methylated Transgenes," Mol. Gen. Genet., 244:219–229 (1994), which are hereby incorporated by reference) and integration position of transgenes (position effect) in the genome (Peach et al., "Transgene Expression Variability (Position Effect) of CAT and GUS Reporter Genes Driven by Linked Divergent T-DNA Promoters," Plant. Mol. Biol., 17:49–60 (1991); Bhattacharyya et al., "Reduced Variation in Transgene Expression From a Binary Vector With Selectable Markers at the Right and Left T-DNA Borders," Plant J., 6:957–968 (1994), which are hereby incorporated by reference). Thus, it is difficult to conclude which type of promoter complex (either one copy of ABRC1 or four copies of ABRC1) would be better for generation of stress-tolerant transgenic rice plants. According to the above results, 4 copies of ABRC1-containing promoter complex is preferred because it can give approximately 50% to 200% higher GUS activity (e.g., plant L7) than one copy of ABRC1-containing promoter complex (plant L5). The stress-induced expression vectors can be used to construct plasmids containing other potentially useful genes for transformation of rice. Transgenic rice plants with foreign genes driven by a stress-induced promoter are expected to develop and grow better than using a constitutive promoter because the transgenes would be highly expressed only under stress conditions.

Since it is well established that environmental stresses, such as water deficit and salinity, usually lead to enhanced levels of endogenous ABA (Zeevaart et al., "Metabolism and Physiology of Abscisic Acid," Annu. Rev. Plant Physiol. Plant Mol. Biol., 39:439–473 (1988), which is hereby incorporated by reference), it was reasoned that an ABA responsive promoter could also be induced by stress conditions. Indeed, the ABA responsive gene constructs tested above were all induced by water deficit and NaCl treatment. For an ABA/stress responsive promoter to be useful in driving the expression of useful genes, it is better to be highly sensitive and respond quickly to ABA/stress. Indeed, it has been shown that ABRC1/actin minimal promoter responds to mild water stress and salinity within a couple of days (Tables 9 and 10). Although not determined in the Examples above, it is believed that this construct is even more sensitive, because Shen et al. (Shen et al., "Hormone Response Complex of a Novel Abscisic Acid and Cycloheximide Inducible Barley Gene," *J. Biol. Chem.*, 268:23652–23660 (1993), which is hereby incorporated by reference) have shown that HVA22, whose promoter contains ABRC1, is responsive to ABA concentrations as low as $10^{-8}$M, and this gene is induced by $10^{-6}$ M ABA within 40 minutes. Therefore, ABRC1 appears to have the desirable features in regulating transgenes encoding useful traits for protecting plants against stress conditions.

Among the ABA responsive promoter sequences, ABRC as defined by Shen and Ho (Shen et al., "Functional Dissection of an Abscisic Acid (ABA)-Inducible Gene Reveals Two Independent ABA-Responsive Complexes Each Containing a G-box and a Novel cis-Acting Element," *The Plant Cell*, 7:295–307 (1995), which is hereby incorporated by reference) and Shen et al (Shen et al., "Modular Nature of Abscisic Acid (ABA) Response Complexes: Composite Promoter Units that are Necessary and Sufficient for ABA Induction of Gene Expression in Barley," *The Plant Cell*, 8:1107–1119 (1996), which is hereby incorporated by reference) appear to be necessary and sufficient for a high level of ABA induction. However, their work was essentially carried out in a highly specialized tissue, the aleurone layers of germination barley seeds. By linking ABRC to a minimal promoter derived from actin gene which is constitutively expressed in many cell types, it has been shown that gene constructs can be expressed in at least two major vegetative tissues, leaves and roots, in addition to the aleurone layers. Although the transgenic approach as described above has proven to be an efficient means to analyze promoters, ectopic functions of promoters in transgenic plants have also been observed. For example, Sieburth and Meyerowitz (Sieburth et al., "Molecular Dissection of the AGAMOUS Control Region Show that cis Elements for Spatial Regulation are Located Intragenically," *Plant Cell*, 9:355–365 (1997), which is hereby incorporated by reference) have recently reported that the cis elements for spatial regulation of the *Arabidopsis* AGAMOUS gene are located intragenically. Thus, it is conceivable that the promoter of a gene does not always contain all the elements regulating its expression. However, it is clear from the Examples above and from the work of Shen and Ho (Shen et al., "Modular Nature of Abscisic Acid (ABA) Response Complexes: Composite Promoter Units that are Necessary and Sufficient for ABA Induction of Gene Expression in Barley," *The Plant Cell*, 8:1107–1119 (1996), which is hereby incorporated by reference) that ABRC1 alone is sufficient to confer a high level of ABA inducibility. It is equally significant that the gene constructs tested in this study function well in both rice and barley. Since the ABRC used was derived from a barley gene with homologs present in many cereal grains, it is conceivable that the gene constructs could work in other cereals as well.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for conferring tolerance to salt stress and drought stress in a monocotyledonous plant comprising:
   transforming the monocotyledonous plant with a plasmid comprising a DNA molecule that increases tolerance to salt stress and drought stress in plants, wherein the plasmid is selected from the group consisting of pJS112, pJP21, and pJPM001; and
   expressing the DNA molecule in the monocotyledonous plant to confer tolerance to salt stress and drought stress in the plant.

2. The method according to claim 1, wherein the monocotyledonous plant is selected from the group consisting of rice, wheat, maize, barley, oat, rye, millet, and sorghum.

3. The method according to claim 2, wherein the monocotyledonous plant is rice.

4. The method according to claim 1, wherein said transforming comprises:
   propelling particles at cells of the monocotyledonous plant under conditions effective for the particles to penetrate into the cell interior and
   introducing the plasmid into the cell interior.

5. The method according to claim 4, wherein the plasmid is associated with the particles, whereby the plasmid is carried into the cell interior together with the particles.

6. The method according to claim 4, wherein the plasmid surrounds the cell and is drawn into the cell interior with the particles.

7. The method according to claim 1, wherein said transforming comprises:
   contacting tissue of the monocotyledonous plant with an inoculum of a bacterium of the genus *Agrobacterium*, wherein the bacterium is transformed with the plasmid.

8. The method according to claim 7, wherein the bacterium of the genus *Agrobacterium* is *Agrobacterium tumefaciens*.

9. The method according to claim 7, wherein the tissue is selected from protoplasts, cells, or calli derived from mature embryo or immature embryo of rice, wheat, maize, barley, oat, rye, millet, or sorghum.

10. The method according to claim 1, wherein the plasmid is pJS112.

11. The method according to claim 1, wherein the plasmid is pJP21.

12. The method according to claim 1, wherein the plasmid is pJPM001.

* * * * *